U S009936795B2

(12) United States Patent
Moskovich et al.

(10) Patent No.: US 9,936,795 B2
(45) Date of Patent: Apr. 10, 2018

(54) TOOTHBRUSH

(71) Applicant: COLGATE-PALMOLIVE COMPANY, New York, NY (US)

(72) Inventors: Robert Moskovich, East Brunswick, NJ (US); Kelly Gail Duncan, Washington, NJ (US); Matthew Lee Kolb, Upper Black Eddy, PA (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/106,394

(22) PCT Filed: Dec. 18, 2013

(86) PCT No.: PCT/US2013/076152
§ 371 (c)(1),
(2) Date: Jun. 20, 2016

(87) PCT Pub. No.: WO2015/094230
PCT Pub. Date: Jun. 25, 2015

(65) Prior Publication Data
US 2017/0000252 A1  Jan. 5, 2017

(51) Int. Cl.
*A61C 19/06* (2006.01)
*A46B 11/00* (2006.01)
(Continued)

(52) U.S. Cl.
CPC ............ *A46B 11/001* (2013.01); *A46B 5/021* (2013.01); *A46B 9/04* (2013.01); *A46B 15/0004* (2013.01);
(Continued)

(58) Field of Classification Search
CPC ............................ A46B 11/001; A61C 19/066
(Continued)

(56) References Cited

U.S. PATENT DOCUMENTS 5,713,738 A    2/1998  Yarborough
6,162,055 A   12/2000  Montgomery et al.
(Continued)

FOREIGN PATENT DOCUMENTS

DE         20319405      3/2005
DE       202004001004    3/2005
WO     WO 2007/102678    9/2007

OTHER PUBLICATIONS

Corresponding International Search Report for PCT/US2013/076152 dated Sep. 9, 2014.
(Continued)

*Primary Examiner* — David Walczak
*Assistant Examiner* — Joshua Wiljanen

(57) ABSTRACT

A toothbrush comprising a body comprising a handle portion, a head portion and a longitudinal axis; a plurality of tooth cleaning elements extending from the head portion; a depression formed in an outer surface of the handle portion of the body, the depression comprising a floor; a power source disposed within the body; an electromagnetic radiation (EMR) source disposed within the handle portion and operably coupled to the power source, the EMR source configured to emit EMR from the floor of the depression; and a cover coupled to the handle portion so as to be alterable between: (1) a storage state in which the depression is enclosed by the cover; and (2) a use state in which the floor of the depression is exposed.

15 Claims, 16 Drawing Sheets

(51) Int. Cl.
| | |
|---|---|
| *A46B 15/00* | (2006.01) |
| *A46B 5/02* | (2006.01) |
| *A61C 17/22* | (2006.01) |
| *A61N 1/40* | (2006.01) |
| *A61N 5/04* | (2006.01) |
| *A61N 5/10* | (2006.01) |
| *A46B 9/04* | (2006.01) |
| *A61N 5/06* | (2006.01) |
| *A61C 5/90* | (2017.01) |

(52) U.S. Cl.
CPC ........ *A46B 15/0034* (2013.01); *A61C 17/227* (2013.01); *A61C 19/066* (2013.01); *A61N 1/40* (2013.01); *A61N 5/045* (2013.01); *A61N 5/062* (2013.01); *A61N 5/0603* (2013.01); *A61N 5/0624* (2013.01); *A61N 5/10* (2013.01); *A46B 9/045* (2013.01); *A46B 2200/1066* (2013.01); *A61C 5/90* (2017.02); *A61N 2005/0606* (2013.01); *A61N 2005/0644* (2013.01); *A61N 2005/0659* (2013.01); *A61N 2005/0661* (2013.01); *A61N 2005/0662* (2013.01)

(58) Field of Classification Search
USPC .......................................... 401/198, 199, 202
See application file for complete search history.

(56) References Cited

U.S. PATENT DOCUMENTS

| | | | |
|---|---|---|---|
| 6,254,388 | B1 | 7/2001 | Yarborough |
| 6,343,933 | B1 | 2/2002 | Montgomery et al. |
| 6,416,319 | B1 | 7/2002 | Cipolla |
| 7,261,558 | B2 | 8/2007 | Rizoin et al. |
| 8,241,035 | B2 | 8/2012 | Jones et al. |
| 2005/0064371 | A1 | 3/2005 | Soukos et al. |
| 2006/0240375 | A1 | 10/2006 | Soukos et al. |
| 2007/0003905 | A1 | 1/2007 | Nguyen et al. |
| 2007/0111167 | A1 | 5/2007 | Russell et al. |
| 2008/0254405 | A1 | 10/2008 | Montgomery et al. |
| 2010/0296859 | A1 | 11/2010 | Lerner et al. |
| 2011/0091835 | A1 | 4/2011 | Levine |
| 2013/0227803 | A1 | 9/2013 | Russell et al. |

OTHER PUBLICATIONS

International Search Report and the Written Opinion of the International Searching Authority issued in International Application PCT/US2013/076152 dated Sep. 18, 2014.

TOOTHBRUSH

BACKGROUND

Oral care implements such as toothbrushes are typically used by applying toothpaste or dentifrice to a bristle section on the head of the toothbrush, followed by brushing regions of the oral cavity (e.g., the teeth or soft tissue such as the tongue and/or gums) with the bristle section. Furthermore, a growing cosmetic trend has been to whiten the teeth because white teeth are generally associated with a healthy and clean oral cavity. However, conventional teeth whitening requires a user to make multiple visits to a dentist or to apply a whitening solution to a tray and to then leave the tray in the user's mouth for a period of time. While tray-based systems are suitable, many people do not use them due to the fact that they tend to be uncomfortable and/or awkward. Moreover, in order to use a whitening tray, a user must keep the tray and the required components at hand. This not only requires extra storage space in already cramped bathroom cabinets, but also requires that the user remember to use the whitening system. Furthermore, these tray-based systems are not conveniently portable for transport and/or travel. These problems require a better way to deliver the whitening agent (and other oral care agents) to the teeth and a more convenient tooth whitening (and other oral care agent application) system for transport and/or travel.

BRIEF SUMMARY

Exemplary embodiments according to the present disclosure are directed to a toothbrush having a body and a treatment device coupled to the body. The treatment device comprises a housing, a power source and an electromagnetic radiation source. The treatment device may be alterable between a storage state and a use state. In other embodiments, the power source and the electromagnetic radiation source may be formed into the body and protected by a cover when not in use.

In one embodiment, the invention can be a toothbrush comprising: a body comprising a handle portion, a head portion and a longitudinal axis; a plurality of tooth cleaning elements extending from the head portion; a depression formed in an outer surface of the handle portion of the body, the depression comprising a floor; a power source disposed within the body; an electromagnetic radiation (EMR) source disposed within the handle portion and operably coupled to the power source, the EMR source configured to emit EMR from the floor of the depression; and a cover coupled to the handle portion so as to be alterable between: (1) a storage state in which the depression is enclosed by the cover; and (2) a use state in which the floor of the depression is exposed.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
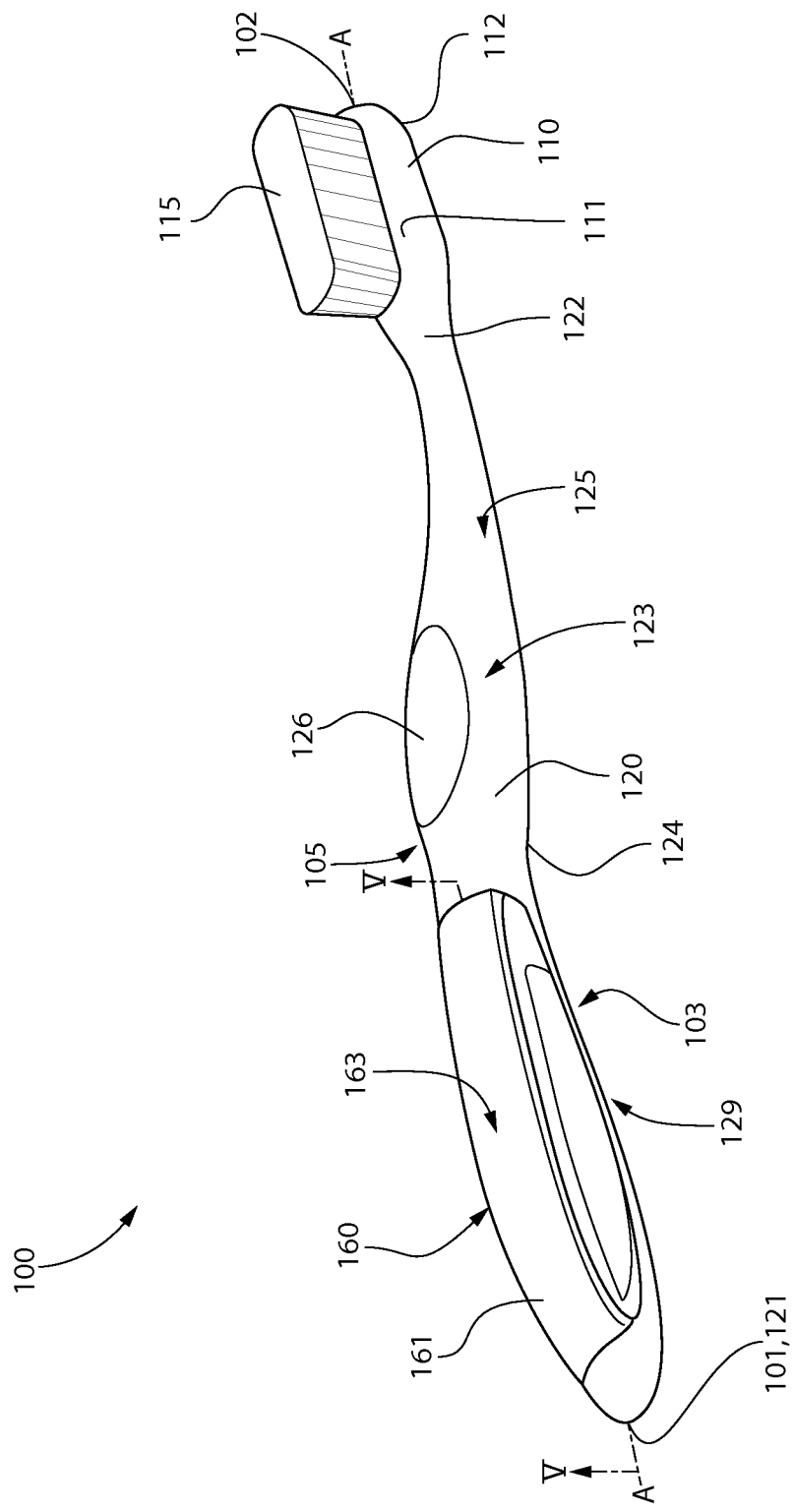
FIG. 1 is a perspective view of a toothbrush having a body and a treatment device coupled thereto in accordance with a first embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Figure 2:
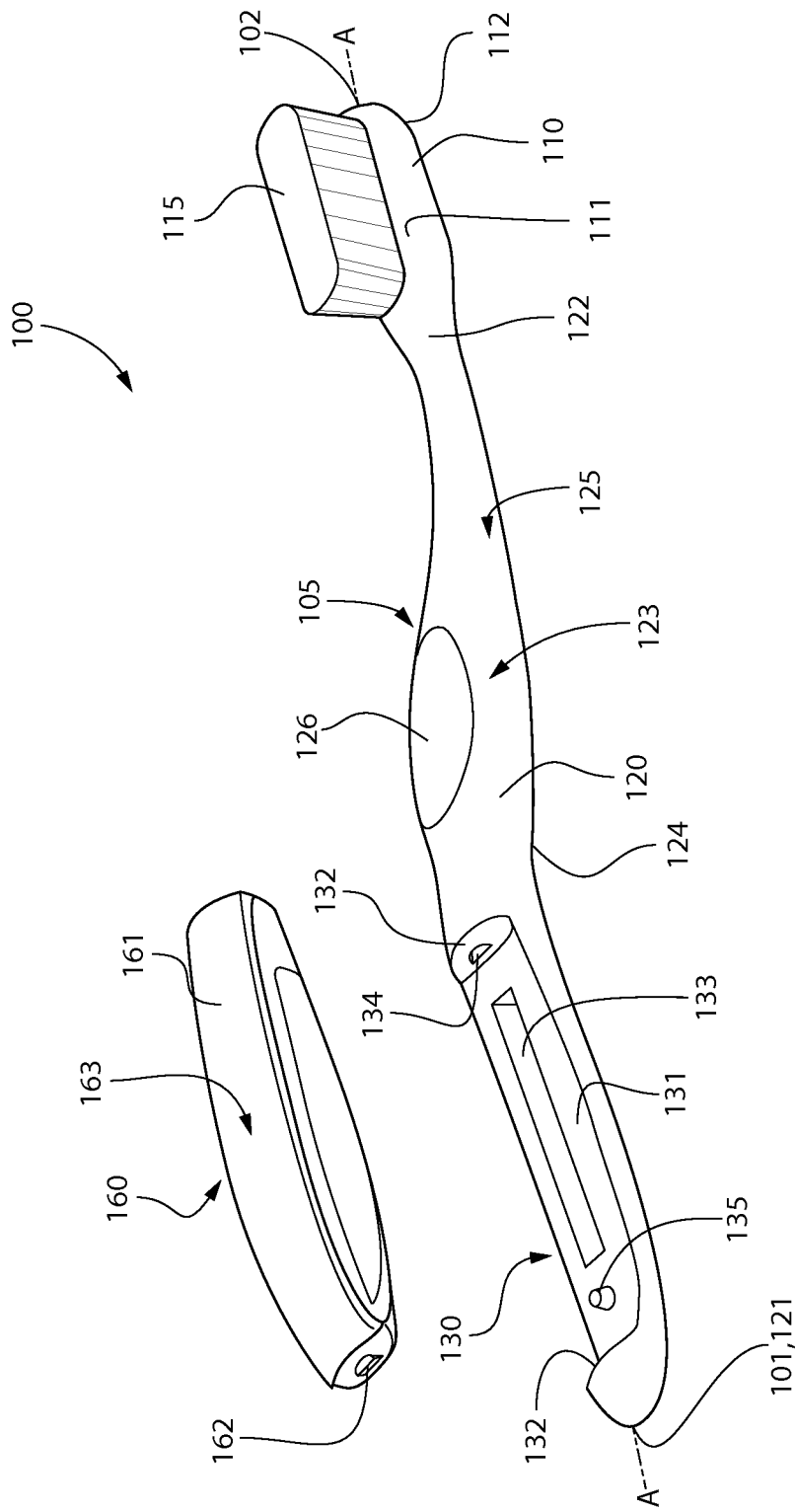
FIG. 2 is a perspective view of the toothbrush of FIG. 1 with the treatment device separated from the body.

Referring first to FIGS. 1 and 2 concurrently, an oral care implement 100 is illustrated in accordance with an embodiment of the present invention. The oral care implement 100 generally comprises a body 105 comprising a handle portion 120 and a head portion 110, tooth cleaning elements 115 extending from the head portion 110, and a treatment device 160 coupled to the body 105. The oral care implement 100 is intended to be used such that the tooth cleaning elements 115 clean a user's teeth. Furthermore, the treatment device 160 is intended to be used to emit electromagnetic radiation (EMR) to a user's teeth or other oral surfaces. Specifically, before or after brushing his or her teeth with the oral care implement, the user can apply an oral care material, such as for example without limitation a tooth whitening solution, to the user's teeth. Then, after the oral care material is applied to the user's teeth, the user can emit EMR to the user's teeth using the treatment device. Emitting EMR to the user's teeth after applying, for example, a tooth whitening solution to the user's teeth may enhance the effects of the tooth whitening solution by speeding up the tooth whitening process or by increasing the degree to which the tooth whitening solution is able to whiten the user's teeth. EMR may also increase the effects and benefits of oral care materials other than tooth whitening solutions. In the inventive oral care implement 100 described herein, the treatment device 160 is coupled to the body 105 of the oral care implement 100 so that the brushing and whitening processes can be achieved with a single, portable oral care implement 100. In some embodiments as discussed in more detail below the oral care material may be contained within the oral care implement 100, such as by being contained within the body 105 of the oral care implement 100 or within the treatment device 160 of the oral care implement 100.

In the exemplified embodiment, the oral care implement 100 is in the form of a manual toothbrush. However, in certain other embodiments the oral care implement 100 can take on other forms such as being a powered toothbrush, a tongue scraper, a gum and soft tissue cleanser, a water pick, an interdental device, a tooth polisher, a specially designed ansate implement having tooth engaging elements or any other type of implement that is commonly used for oral care. Thus, it is to be understood that the inventive concepts discussed herein can be applied to any type of oral care implement unless a specific type of oral care implement is specified in the claims.

The body 105 of the oral care implement 100 generally extends from a proximal end 101 to a distal end 102 along a longitudinal axis A-A. Conceptually, the longitudinal axis A-A is a reference line that is generally coextensive with the three-dimensional center line of the body 105. Because the body 105 may, in certain embodiments, be a non-linear structure, the longitudinal axis A-A of the body 105 may also be non-linear in certain embodiments. However, the invention is not to be so limited in all embodiments and in certain other embodiments the body 105 may have a simple linear arrangement and thus a substantially linear longitudinal axis A-A.

As noted above, the body 105 of the oral care implement 100 generally comprises the head portion 110 and the handle portion 120. The handle portion 120 is an elongated structure extending from a proximal end 121 (which is also the proximal end 101 of the body 105) to a distal end 122. The handle portion 120 provides the mechanism by which the user can hold and manipulate the oral care implement 100 during use. The handle portion 120 comprises an outer surface 125 that includes a front surface 123 and an opposing rear surface 124. In the exemplified embodiment, the handle portion 120 is generically depicted having various contours for user comfort. Of course, the invention is not to be so limited in all embodiments and in certain other embodiments the handle portion 120 can take on a wide variety of shapes, contours and configurations, none of which are limiting of the present invention unless so specified in the claims. In one particular embodiment, the handle portion 120 has a generally cylindrical shape.

In the exemplified embodiment, the handle portion 120 is formed of a rigid plastic material, such as for example without limitation polymers and copolymers of ethylene, propylene, butadiene, vinyl compounds and polyesters such as polyethylene terephthalate. In other embodiments the handle portion 120 can be formed of any material that is not incompatible with an oral care material that is stored therein. Of course, the invention is not to be so limited in all embodiments and the handle portion 120 may include a resilient material, such as a thermoplastic elastomer, as a grip cover that is molded over portions of or the entirety of the handle portion 120 to enhance the gripability of the handle portion 120 during use. For example, portions of the handle portion 120 that are typically gripped by a user's palm during use may be overmolded with a thermoplastic elastomer or other resilient material to further increase comfort to a user.

The head portion 110 of the oral care implement 100 is coupled to the handle portion 120 and comprises a front surface 111 and an opposing rear surface 112. Specifically, the head portion 110 of the oral care implement 100 is coupled to the distal end 122 of the handle portion 120. In the exemplified embodiment, the head portion 110 is formed integrally with the handle portion 120 as a single unitary structure using a molding, milling, machining or other suitable process. Thus, in such embodiments the body 105 including both the handle portion 120 and the head portion 110 is formed from a single shot in an injection molding process or in any other manner known in the art. However, in other embodiments the handle portion 120 and the head portion 110 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. Typically, the head portion 110 is formed of any of the materials described above for use in forming the handle portion 120.

In the exemplified embodiment, the head portion 110 of the oral care implement 100 is provided with a plurality of tooth cleaning elements 115 extending from the front surface 111. In the exemplified embodiment the tooth cleaning elements 115 are generically illustrated. In certain embodiments the exact structure, pattern, orientation and material of the tooth cleaning elements 115 are not to be limiting of the present invention. Thus, as used herein, the term "tooth cleaning elements" is used in a generic sense to refer to any structure that can be used to clean, polish or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth cleaning elements 115 of the present invention can be connected to the head portion 110 in any manner known in the art. For example, staples/anchors, in-mold tufting (IMT) or anchor free tufting (AFT) could be used to mount the cleaning elements/tooth engaging elements to the head portion 110. In certain embodiments, the invention can be practiced with various combinations of stapled, IMT or AFT bristles. In AFT, a plate or membrane having tuft holes therein is formed separately from the body 105 of the oral care implement 100. Bristles or other tooth cleaning elements are positioned within the tuft holes. The free ends of the bristles on one side of the plate or membrane perform the cleaning function. The ends of the bristles on the other side of the plate or membrane are melted together by heat to be anchored in place. After the bristles are properly coupled to the head plate, the head plate is secured to the brush head such as by ultrasonic welding. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

Although not illustrated herein, in certain embodiments the head portion 110 may also include a soft tissue cleanser coupled to or positioned on its rear surface 112. An example of a suitable soft tissue cleanser that may be used with the present invention and positioned on the rear surface 112 of the head portion 110 is disclosed in U.S. Pat. No. 7,143,462, issued Dec. 5, 2006 to the assignee of the present application, the entirety of which is hereby incorporated by reference. In certain other embodiments, the soft tissue cleanser may include protuberances, which can take the form of elongated ridges, nubs, or combinations thereof. Of course, the invention is not to be so limited and in certain embodiments the oral care implement 100 may not include any soft tissue cleanser.

Still referring to FIGS. 1 and 2 concurrently, the oral care implement 100 will be further described. As discussed above, in addition to the body 105, the oral care implement 100 also comprises the treatment device 160, which is coupled to the body 105. The treatment device 160 functions to emit electromagnetic radiation (EMR) to a user's oral cavity as will be discussed in more detail below with reference to FIGS. 3 and 4. More specifically, the treatment device 160 is coupled to the body 105 so as to be alterable between a storage state (FIG. 1) and a use state (FIG. 2). In the exemplified embodiment, the treatment device 160 is detachably coupled to the body 105 such that the treatment device 160 can be completely separated from the body 105 when the treatment device 160 is in the use state as depicted in FIG. 2. However, the invention is not to be so limited in all embodiments and in certain other embodiments the treatment device 160 may be coupled to the body 105 in both the storage and use states, such as by being attached by a hinge or the like so that the treatment device 160 is hingedly or pivotally coupled to the body 105, or such as being slidably coupled to the body 105 so that the treatment device 160 can be translated longitudinally between the storage and use states.

The handle portion 120 of the body 105 comprises a longitudinal depression 130 formed therein. In the exemplified embodiment, the longitudinal depression 130 is located in a proximal section 103 of the handle portion 120. More specifically, the longitudinal depression 130 is located adjacent the proximal end 121 of the handle portion 120 and extends to a location adjacent a thumb grip portion 126 of the handle portion 120. However, the invention is not to be so limited in all embodiments and the longitudinal depression 130 may be positioned at other locations along the handle portion 120 of the body 105 and may extend for longer or shorter lengths along the handle portion 120. Furthermore, although in the exemplified embodiment the longitudinal depression 130 is illustrated as being formed into the front surface 123 of the handle portion 120, the invention is not to be so limited in all embodiments and in certain other embodiments the longitudinal depression 130 may be formed into the rear surface 124 of the handle portion 120 or any portions (such as side surfaces) of the outer surface 125 of the handle portion 120 as desired. In other embodiments the longitudinal depression 130 may be located on the rear surface 112 of the head portion 110. In the exemplified embodiment, the longitudinal depression 130 forms a recess or cutout into the outer surface 125 of the handle portion 120 within which the treatment device 160 nests when the treatment device 160 is in the storage state.

The longitudinal depression 130 comprises a floor 131 and upstanding sidewalls 132 that extend from the floor 131 to the outer surface 125 of the handle portion 120. Furthermore, a slot or aperture 133 is formed into the floor 131 of the longitudinal depression 130. The aperture 133 is longitudinally elongated along the floor 131 of the longitudinal depression 130. Furthermore, in the exemplified embodiment the aperture 133 does not extend through the entire thickness of the handle portion 120, but rather the aperture 133 has a floor 136 (see FIG. 5). However, the invention is not to be so limited in all embodiments and in certain other embodiments the aperture 133 may extend through the entire thickness of the handle portion 120 (i.e., from the front surface 123 to the rear surface 124) so as to form a passageway through the handle portion 120. The purpose of the aperture 133 will be better understood from the description of FIG. 5, but it is intended to house a portion of the treatment device 160 when the treatment device 160 is in the storage state. In certain embodiments, the aperture 133 may not be needed for housing a portion of the treatment device 160 and therefore the aperture 133 may be omitted in some embodiments.

In the exemplified embodiment, the longitudinal depression 130 further includes at least one connector 134 on the upstanding sidewalls 132 for coupling the treatment device 160 to the handle portion 120. Although only one connector 134 is visible in FIG. 2, it can be seen from FIG. 5 that in the exemplified embodiment there is a connector 134 on each of the opposing sidewalls 132. Of course, the number and exact location of the connectors 134 are not to be limiting in all embodiments. Furthermore, in the exemplified embodiment the connector 134 is an opening or notch. Of course, the invention is not to be so limited in all embodiments and in certain other embodiments the connector 134 can be a bump or protrusion. In still other embodiments the connector 134 can be a part of a hook-and-loop fastener system or any other type of mechanical coupling system or device. Regardless of the exact configuration of the connectors 134, they are intended to enable coupling between the treatment device 160 and the handle portion 120.

In that regard, the treatment device 160 comprises a housing 161 that is couplable to the body 105 of the toothbrush 100 and that houses various other components as will be discussed below with reference to FIGS. 3 and 4. In the exemplified embodiment, the treatment device 160 comprises a connector 162 on the housing 161. In the exemplified embodiment, the connector 162 is a protrusion that is intended to mate with the connector 134 (i.e., the opening or notch) on the sidewall 134 of the longitudinal depression 130. Of course, in other embodiments the connector 134 may be the protrusion as discussed above and the connector 162 may be a notch or opening.

In certain embodiments, the entire housing 161, including the connector 162, is formed of a rigid plastic material, such as any of the materials discussed above with regard to the handle portion 120. However, due to its small size, the connector 162 is able to have some resiliency/movement to enable the treatment device 160 to be coupled to and decoupled from the handle portion 120 of the body 105. Specifically, when positioning the treatment device 160 into and out of the storage state, the connector 162 may move and flex as needed to enable the treatment device 160 to nest within and be separated from the handle portion 120 of the body 105.

Furthermore, in the exemplified embodiment the longitudinal depression 130 of the handle portion 120 of the body 105 comprises a protuberance 135 extending upwardly from the floor 131. The protuberance 135 is intended to mate with an opening and switch on the treatment device 160 as will be described in more detail below with reference to FIGS. 3-5.

When the treatment device 160 is coupled to the handle portion 120 in the storage state, the treatment device 160 nests within the longitudinal depression 130. Furthermore, in the storage state the housing 161 of the treatment device 160 forms a transverse section of a handle 129 of the toothbrush 100 along the length of the longitudinal depression 130. Thus, together the treatment device 160 and the handle portion 120 of the body 105 form a handle 129 for the toothbrush 100. Furthermore, in certain exemplary embodiments an outer surface 163 of the housing 161 of the treatment device 160 is substantially flush with the outer surface 125 of the handle portion 120 of the body 105 when the treatment device 160 is in the storage state. The housing 161 of the treatment device 160 also comprises an inner surface 167 (FIG. 4) and the inner surface 167 of the housing 161 is embedded in the handle 129 of the toothbrush 100 when the treatment device 160 is in the storage state. Thus, when the treatment device 160 is in the storage state, the inner surface 167 of the housing 161 is not visible or exposed.

Figure 3:
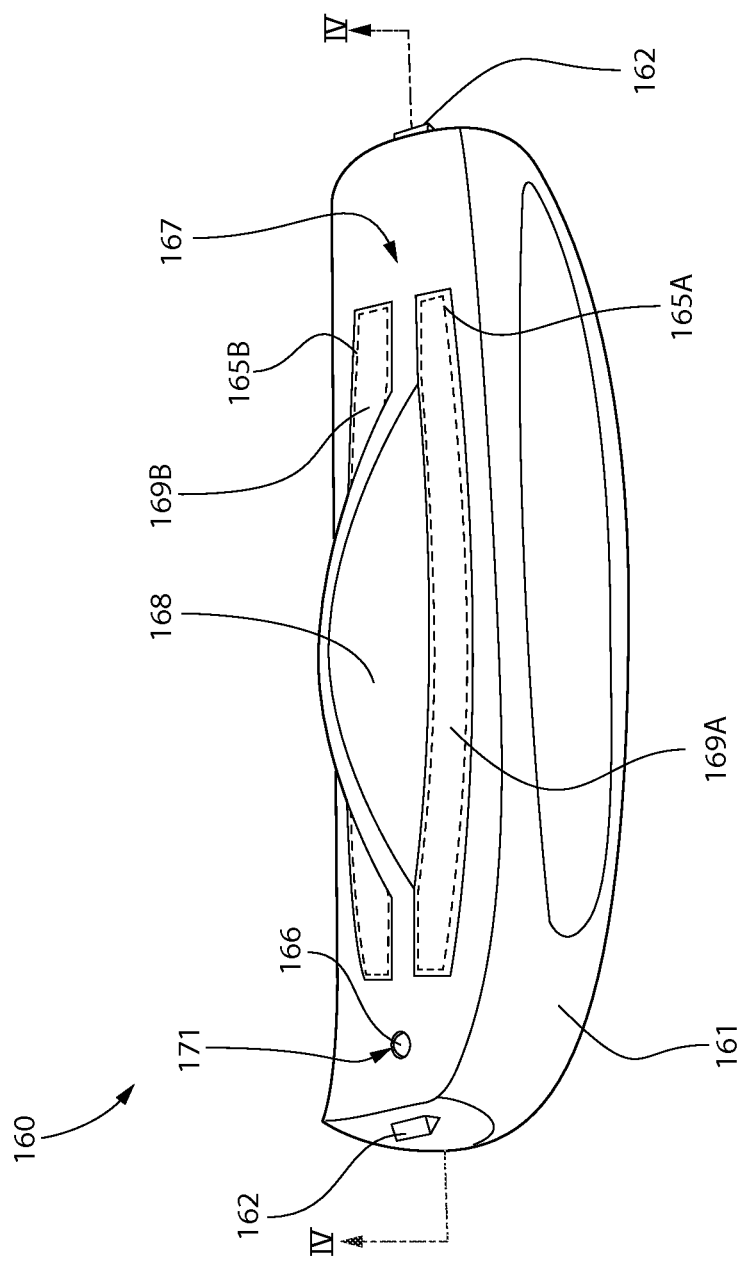
FIG. 3 is a perspective view of the treatment device of FIG. 1.
Figure 4:
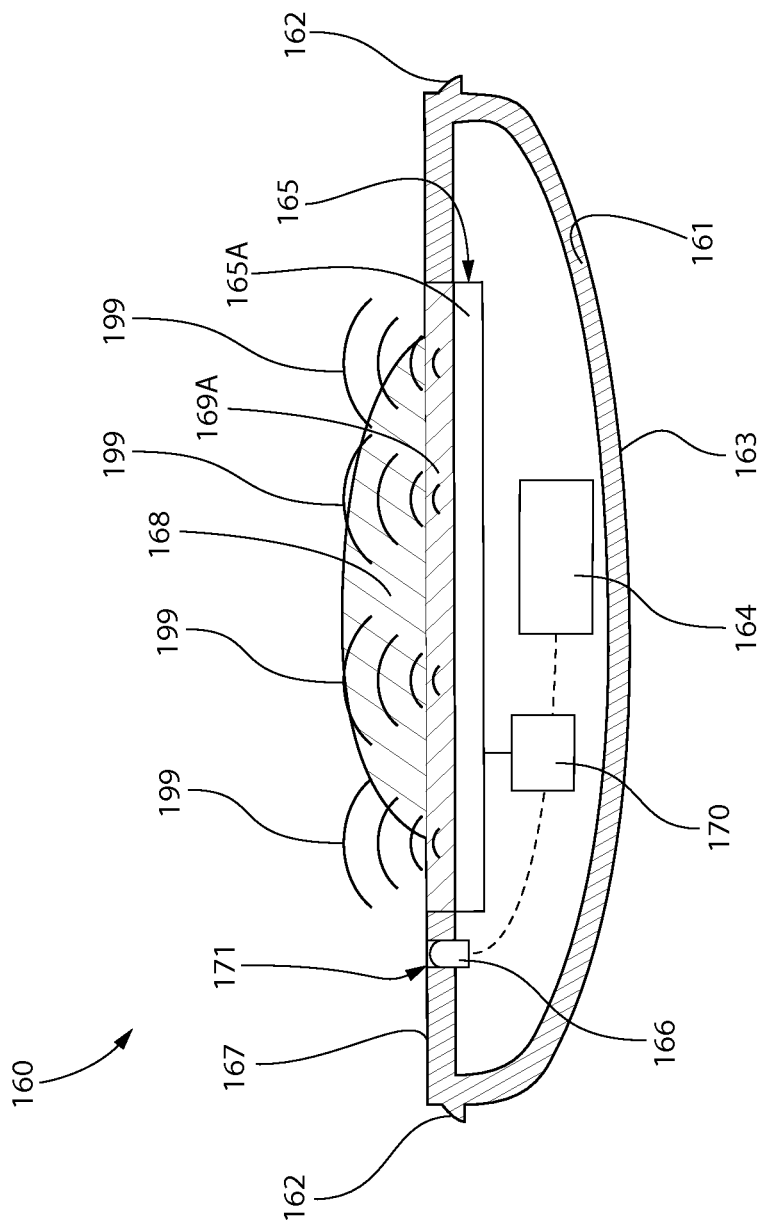
FIG. 4 is a schematic cross-sectional view taken along line IV-IV of FIG. 3.

Referring now to FIGS. 3 and 4 concurrently, the treatment device 160 will be described in more detail. As discussed above, the treatment device 160 comprises the housing 161. Furthermore, a power source 164 and an electromagnetic radiation (EMR) source 165 are disposed within the housing 161. In certain embodiments, the EMR source 165 comprises a first EMR source portion 165A and a second EMR source portion 165B. The EMR source 165 is operably coupled to the power source 164 to provide power to the EMR source 165. The power source 164 can be any type of power source including without limitation batteries and the like. Furthermore, in the exemplified embodiment the treatment device 160 also comprises a switch 166. The switch 166 is operably coupled to the EMR source 165 and to the power source 164 to turn the EMR source 165 on and off. Specifically, when the switch 166 is open power is prevented from transmitting from the power source 164 to the EMR source 165 and the EMR source 165 is in an off state and when the switch 166 is closed power transmits from the power source 164 to the EMR source 165 and the EMR source 165 is in an on state. In the exemplified embodiment, each of the power source 164, the EMR source 165 and the switch 166 is operably coupled together via a controller or processor 170. However, in other embodiments the processor 170 may be omitted and other operable couplings between the various electronic components are possible.

The EMR source 165 is intended to emit electromagnetic radiation. The term electromagnetic radiation includes any type of radiation on the electromagnetic radiation spectrum. Specifically, in some embodiments electromagnetic radiation includes radiowaves, microwaves, infrared, visible light, ultraviolet, X-rays and gamma rays. In certain embodiments the electromagnetic radiation is preferably ultraviolet radiation, such as that having a wavelength of 150-410 nm, more specifically 200-410 nm, still more specifically 250-410 nm, even more specifically 300-410 nm, and still more specifically 350-410 nm. Of course, the invention is not to be particularly limited by the type of radiation emitted by the EMR source 165 in all embodiments and waves that are longer than 410 nm or shorter than 350 nm can be used in other embodiments. Thus, in other embodiments the electromagnetic radiation may be substantially free of ultraviolet radiation. In other embodiments the electromagnetic radiation may comprise wavelengths within a range of about 300 nm to about 750 nm. A person of ordinary skill in the art will be able to determine the most preferred wavelength of the radiation to be emitted from the EMR source 165 to achieve desired functions, such as tooth whitening as discussed in more detail below. The EMR source 165 may be light bulbs that emit the desired radiation, such as UV bulbs, LEDs or the like in certain embodiments. Whatever form of source is used and whatever the size of the wavelengths, care should be taken to control the intensity of the radiation in order to avoid possible negative health effects.

As discussed above, the housing 161 of the treatment device 160 comprises an inner surface 167. Furthermore, the treatment device 160 comprises a bite guard 168 that protrudes from the inner surface 167 of the housing 161. In the exemplified embodiment, the bite guard 168 has a semi-circular shape and is integrally formed with the housing 161 of the treatment device 160. However, the invention is not to be so limited and the shape of the bite guard 168 may be other than semi-circular, such as rectangular, triangular or any other polygonal shape. In still other embodiments the bite guard 168 may simply be a thin cylindrical protrusion that extends from the inner surface 167 of the housing 161 that can be gripped between a user's teeth and/or lips during use as will be discussed in more detail below. Thus, the size and/or shape of the bite guard 168 are not to be limiting of the present invention in all embodiments. In certain embodiments it is merely desirable that the bite guard 168 is configured to enable a user to maintain the treatment device 160 in a location adjacent to the user's teeth during tooth whitening or other oral hygiene operations such as by gripping the bite guard 168 between the user's upper and lower teeth or between the user's upper and lower lips. Furthermore, in still other embodiments the bite guard 168 may be altogether omitted. In such embodiments the treatment device 160 can be held up to a user's teeth by a user gripping the outer surface 163 of the housing 161, or by positioning the treatment device 160 within the user's mouth in a similar manner as is done with a mouthguard. Thus, the bite guard 168 is not required to be a part of the treatment device 160 in all embodiments.

Furthermore, although described above as being integrally formed with the housing 161, the invention is not to be so limited and in certain embodiments the bite guard 168 may be a separate component that is coupled to the housing 161. For example, the housing 161 may be formed of a rigid or hard plastic material such as one of the materials discussed above with regard to the handle 120 and the bite guard 168 may be formed of a rubber material, such as a thermoplastic elastomer, an unsaturated rubber or a saturated rubber. In such embodiments, the bite guard 168 can be coupled to the housing 161 via mechanical interlocking features in the molding of the housing 161 and the bite guard 168, or by adhesion, fasteners or the like. Forming the bite guard 168 out of a thermoplastic elastomer (or other rubber material) is desirable in some embodiments because it is more comfortable for a user to grip a thermoplastic elastomer between his or her teeth and/or lips than it is to grip a rigid plastic material between his or her teeth and/or lips.

As noted above, in certain embodiments the EMR source 165 comprises a first EMR source portion 165A and a second EMR source portion 165B. In the exemplified embodiment, each of the first and second EMR source portions 165A, 165B and the bite guard 168 is longitudinally elongated. Furthermore, in the exemplified embodiment the bite guard 168 is located in between the first and second EMR source portions 165A, 165B. Thus, the EMR source 165, and more specifically the first and second EMR source portions 165A, 165B, is configured to emit EMR 199 from the housing 601, and more specifically from the inner surface 167 of the housing 161, at a location adjacent to the bite guard 168. Therefore, if the treatment device 160 is being used to emit EMR to a user's teeth, the user will have the bite guard 168 positioned between his or her teeth. Due to the first and second EMR source portions 165A, 165B being located on opposing sides of the bite guard 168, the first EMR source portion 165A will emit EMR to the user's upper teeth while the second EMR source portion 165B emits EMR to the user's lower teeth when the inner surface 167 of the treatment device 160 is adjacent to the user's teeth and the bite guard 168 is being held between the user's upper and lower teeth.

The inner surface 167 of the housing 161 comprises a first EMR transmissive portion 169A and a second EMR transmissive portion 169B. Each of the first and second EMR transmissive portions 169A, 169B is configured to enable the EMR 199 to be emitted from the first and second EMR source portions 165A, 165B and through the housing 161. More specifically, in the exemplified embodiment the first EMR transmissive portion 169A is positioned adjacent to the first EMR source portion 165A and the second EMR transmissive portion 169B is positioned adjacent to the second EMR source portion 165B. Thus, when the first and second EMR source portions 165A, 165B are in the on state, the EMR 199 transmits from the first EMR source portion 165A through the first EMR transmissive portion 169A and from the second EMR source portion 165B through the second EMR transmissive portion 169B.

The first and second EMR transmissive portions 169A, 169B can be formed of any material that enables the EMR 199 to transmit through the housing 161 at the location of the first and second EMR transmissive portions 169A, 169B. Thus, each of the first and second EMR transmissive portions 169A, 169B may be a transparent material such as to form a window in certain embodiments. In other embodiments the first and second EMR transmissive portions 169A, 169B may be opaque or translucent, but still transmissive to the EMR 199 being transmitted by the first and second EMR source portions 165A, 165B. In other embodiments the first and second EMR transmissive portions 169A, 169B may be thinned regions of the housing 161. In still other embodiments the first and second EMR transmissive portions 169A, 169B may be openings formed through the housing 161 that expose the first and second EMR source portions 165A, 165B.

As discussed above, the treatment device 160 comprises a switch 166 that controls the on and off states of the EMR source 165. In the exemplified embodiment, the switch 166 is located within an opening 171 that is formed into the inner surface 167 of the housing 161 of the treatment device 160. In such embodiments the switch 166 is normally biased into a closed state so that the EMR source 165 is turned on and emitting the EMR 199. However, when the treatment device 160 is placed into the storage state, the protuberance 135 extending from the floor 131 of the longitudinal depression 130 protrudes into the opening 171, contacts the switch 166 and transitions the switch 166 into the off state. Thus, when the treatment device 160 is in the storage state, the switch 166 is always open so that the EMR source 165 is turned off (i.e., not receiving power from the power source 164) and is not emitting the EMR 199. When the treatment device is in the use state, the switch 166 is always closed so that the EMR source 165 is turned on (i.e., receiving power from the power source 164) and emitting the EMR 199.

Although the invention is described herein wherein the switch 166 is one which is biased into a closed position so that the EMR source 165 emits the EMR 199 at any time when the treatment device 160 is in the use state, the invention is not to be so limited in all embodiments. Specifically, in certain other embodiments the housing 161 of the treatment device 160 may include a depressible button switch, a slide switch, or any other type of switch on a surface of the housing 161. Specifically, one of the side surfaces of the housing between the inner and outer surfaces 167, 163, or one of the inner or outer surfaces 167, 163 may include such a depressible button switch or slide switch. In such an embodiment, when the treatment device 160 is in the use state, the user can then press the depressible button switch or slide the slide switch to activate and/or deactivate the EMR source 165 to enable and/or prevent the EMR source 165 from emitting the EMR 199 as desired.

Figure 5:
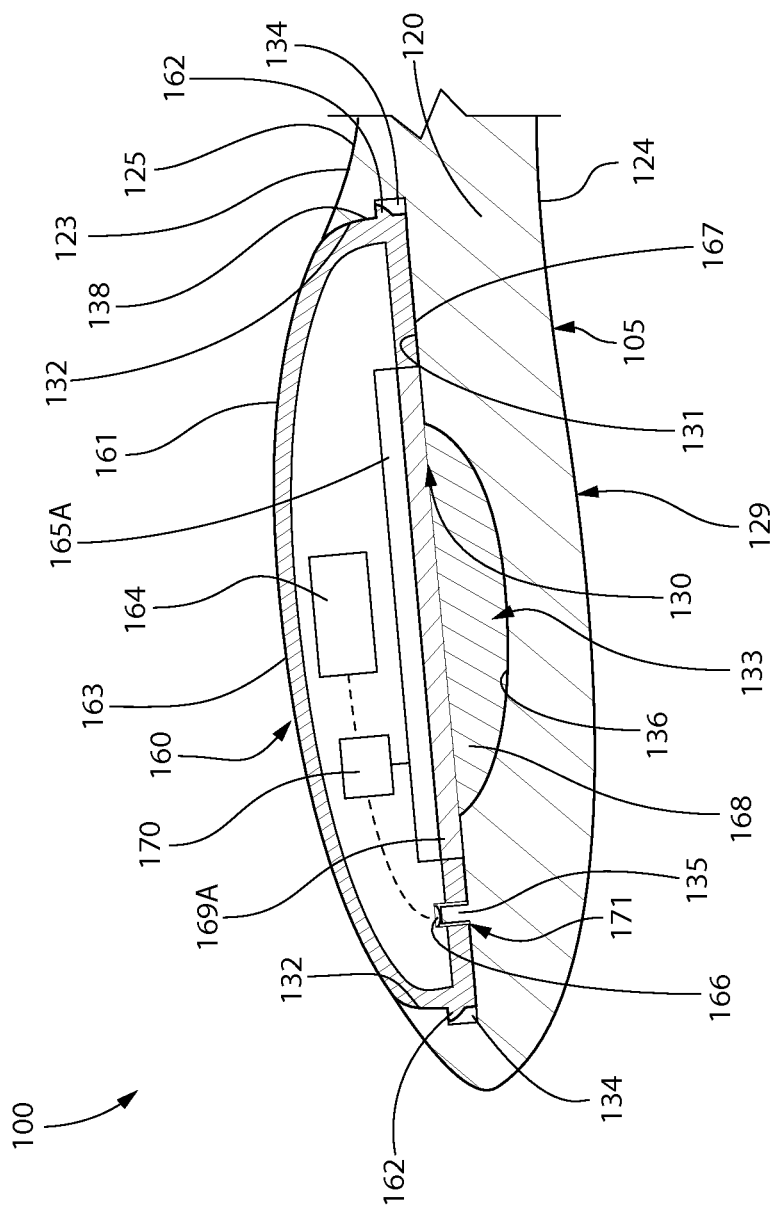
FIG. 5 is a schematic cross-sectional view taken along line V-V of FIG. 1.

Referring to FIG. 5, a schematic longitudinal cross-section of a portion of the oral care implement 100 that includes the treatment device 160 when the treatment device 160 is in the storage state is illustrated. When the treatment device 160 is in the storage state, the treatment device 160 is nested within the longitudinal depression 130 of the handle portion 120 of the body 105. More specifically, the inner surface 167 of the treatment device 160 is positioned adjacent to (and in some embodiments in surface contact with) the floor 131 of the longitudinal depression 130. Furthermore, the bite guard 168 of the treatment device 160 extends into the aperture 133 of the longitudinal depression 130. In the exemplified embodiment, the aperture 133 of the longitudinal depression 130 has a shape that corresponds with the shape of the bite guard 168 so that the distal edge of the bite guard 168 is in contact with the floor 136 of the aperture 133. Of course, the invention is not to be so limited and the aperture 133 can take on any shape that enables the bite guard 168 to be nested therein when the treatment device 160 is in the storage state. In embodiments whereby the bite guard 168 is omitted, the aperture 133 may also be omitted.

Furthermore, when the treatment device 160 is in the storage state, the outer surface 163 of the treatment device 160 is substantially flush with the outer surface 125 of the handle portion 120 such that a smooth continuous transition between the treatment device 160 and the handle portion 120 is achieved. Thus, the handle 129, which comprises the combined handle portion 120 and treatment device 160, is free of ridges and undulations in the transition regions between the treatment device 160 and the handle portion 120, which enhances user comfort when a user is handling the handle 129 of the toothbrush 100.

Furthermore, as discussed above when the treatment device 160 is in the storage state, the protuberance 135 that extends from the floor 131 of the longitudinal depression 130 protrudes into the opening 171 in the treatment device 160 so as to transition the switch 166 from the closed state to the open state. Specifically, the protuberance 135 depresses the switch 166, which causes the switch 166 to enter into the open state so that the EMR source 165 is not emitting the EMR 199. Thus, in accordance with the exemplified embodiment, at all times when the treatment device 160 is in the storage state, the EMR source 165 is powered off because the switch 166 is open. Stated another way, when the treatment device 160 is in the storage state, the switch 166 is automatically maintained or actuated into the open state (such that the EMR source 165 is not emitting the EMR 199). Furthermore, in the exemplified embodiment when the treatment device 160 is in the storage state, the switch 166 is inaccessible and not visible or exposed to a user. Moreover, in accordance with the exemplified embodiment, at all times when the treatment device 160 is in the use state, the EMR source 165 is powered on because the switch 166 is closed. Stated another way, when the treatment device 160 is in the use state, the switch 166 is automatically maintained or actuated into the closed state (such that the EMR source 165 is emitting the EMR 199). Of course, as discussed above alternative structural components for the switch are possible in other embodiments, including conventional button switches, slide switches and the like.

Finally, when the treatment device 160 is in the storage state, the connector 162 of the housing 161 of the treatment device 160 couples with the connector 134 of the handle portion 120 to secure the treatment device 160 in the storage state. More specifically, in the exemplified embodiment the connector 162 of the housing 161 of the treatment device 160, which is a protrusion, nests within the connector 134 of the handle portion 120, which is a notch or opening. The connector 134 further includes a flange 138 that extends above the opening to prevent the protrusion of the housing 161 from easily disengaging or being removed from the opening. Thus, a user must apply some amount of force (i.e., pulling the treatment device 160 and the body 105 in opposite directions) to separate the treatment device 160 from the longitudinal depression 130 due to the corresponding connectors 134, 162. Although a specific structural arrangement of the connectors 134, 162 is illustrated, the invention is not to be limited by the mechanisms used for securing the treatment device 160 to the handle portion 120 in all embodiments, and in other embodiments adhesion, fasteners, hook-and-loop fasteners, springs, other mechanical interlocking features or the like can be used to secure the treatment device 160 to the handle portion 120 in the storage state while enabling the treatment device 160 to be easily transitioned from the storage state to the use state.

The oral care implement 100 is used as follows. The tooth cleaning elements 115 can be used to clean a user's teeth in the normal manner. Either before or after cleaning the user's teeth with the tooth cleaning elements 115 (or at any other desired time), a user may apply an oral care material to the user's teeth. This oral care material may be one that has an efficacy that is increased or activated by the EMR 199 that is generated by the EMR source 165. The specific types of oral care material that may be used are discussed in more detail below. After applying the oral care material to the user's teeth, the treatment device 160 is altered into the use state so that the switch is closed and the EMR source 165 is powered on and emitting the EMR 199 from the housing 161. The user will hold the treatment device 160 up to the user's teeth so that the EMR 199 can be emitted directly to the user's teeth that have been pre-coated with the oral care material. The user may hold the treatment device 160 up to his or her teeth by physically holding the housing 161 with his or her hand or by biting the bite guard 168 so as to hold the bite guard 168 between the user's upper and lower teeth. When positioned as discussed above, the EMR 199 will be emitted directly onto the user's teeth, thereby enhancing the effects of the pre-coated oral care material. After the user has held the treatment device 160 up to his or her teeth for a desired period of time, the user can recouple the treatment device 160 to the body 105 of the oral care implement 100 for storage (i.e., the storage state). Thus, the oral care implement 100 provides a mechanism (i.e., the treatment device 160) for enhancing the benefits/efficacy of an oral care material and that mechanism is provided so as to be couplable to the body 105 of the oral care implement 100.

Figure 6:
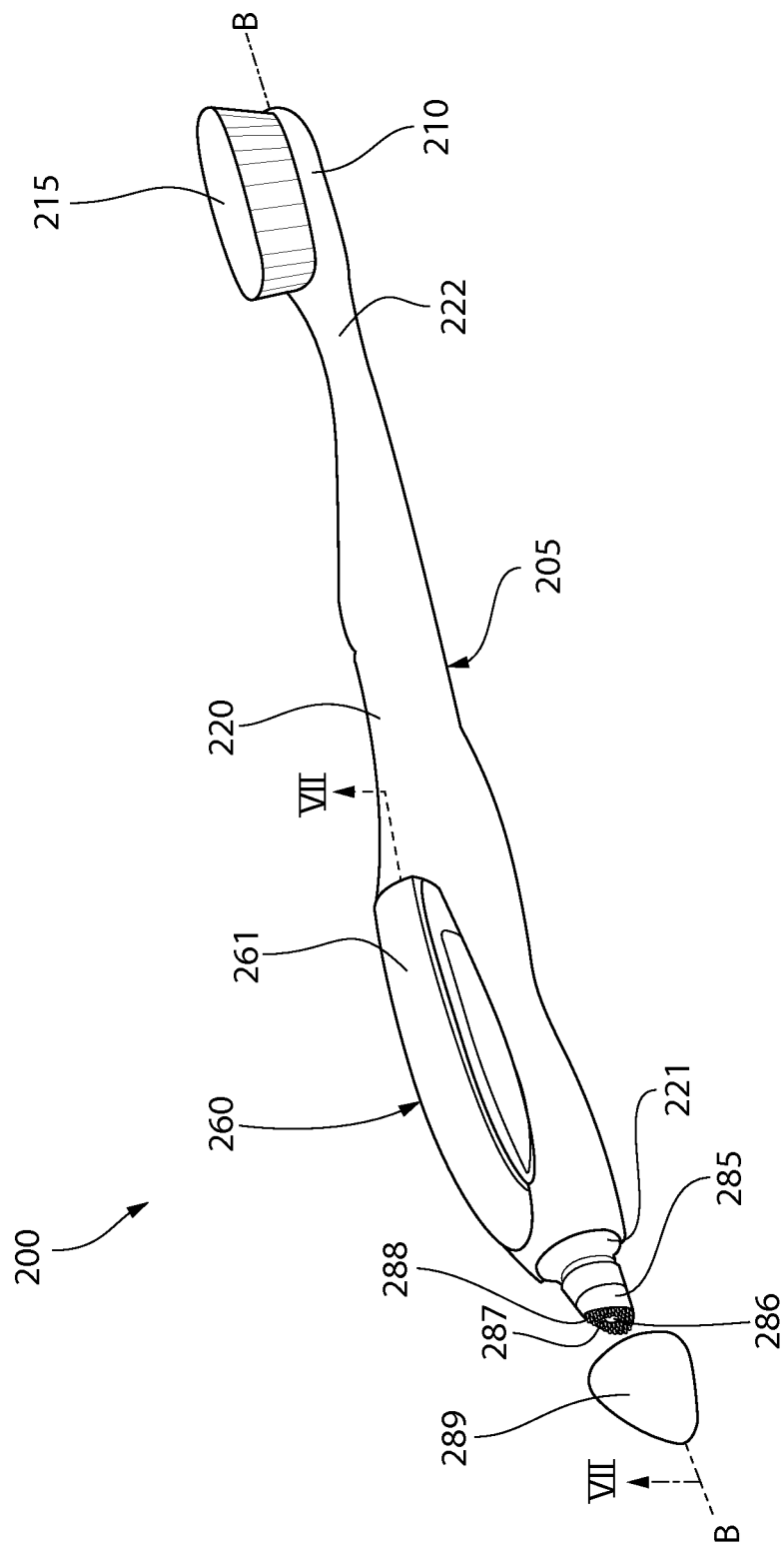
FIG. 6 is a perspective view of a toothbrush having a body and a treatment device coupled thereto in accordance with a second embodiment of the present invention.
Figure 7:
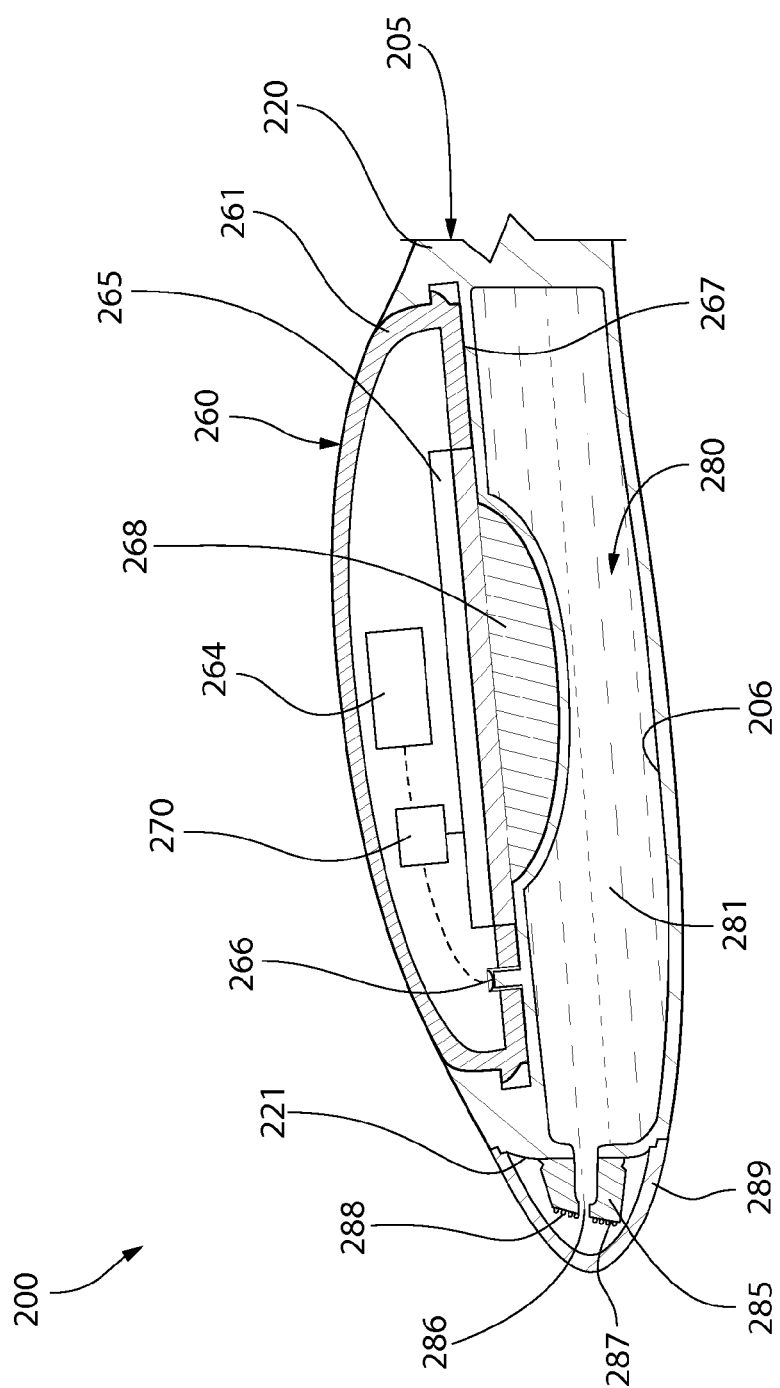
FIG. 7 is a schematic cross-sectional view taken along line VII-VII of FIG. 6 with the cap covering the applicator.

Referring to FIGS. 6 and 7 concurrently, an oral care implement 200 is illustrated in accordance with another embodiment of the present invention. The oral care implement 200 is similar to the oral care implement 100 in many respects, and thus similar features will be similarly numbered except that the 200-series of numbers will be used. Certain features of the oral care implement 200 may be similarly numbered as the oral care implement 100 but might not be described in detail herein in the interest of brevity, it being understood that the discussion of the similar component on the oral care implement 100 applies. Furthermore, features of the oral care implement 100 described above that are not illustrated on the oral care implement 200 or that are illustrated on the oral care implement 200 but not numbered are applicable to the oral care implement 200 in certain embodiments and vice versa. Thus, various combinations of the description below with regard to the oral care implement 200 and the description above with regard to the oral care implement 100 are within the scope of the present invention in some embodiments.

The oral care implement 200 generally comprises a body 205 having a handle portion 220 and a head portion 210 with tooth cleaning elements 215 extending from the head portion 210. More specifically, the handle portion 220 extends from a proximal end 221 to a distal end 222 along a longitudinal axis B-B, and the head portion 210 is coupled to the distal end 222. Furthermore, the oral care implement 200 also comprises a treatment device 260 that is coupled to the body 205. The treatment device 260 is similar to the treatment device 160 and comprises a housing 261 that contains a power source 264, a controller or processor 270, a switch 266 and an EMR source 265 that are operably coupled together. The treatment device 260 also includes a bite guard 268 that extends from an inner surface 267 of the housing 261. The treatment device 260 operates in a similar manner to the treatment device 160 and is coupled to the body 205 in a manner similar to that described above with regard to the treatment device 160.

The main difference between the oral care implement 200 and the oral care implement 100 is that the body 205 of the oral care implement 200 has an inner surface 206 that defines a reservoir or internal cavity 280 for storing a store of oral care material 281. Although the exemplified embodiment illustrates an internal cavity 280 in the body 205, the invention is not to be so limited in all embodiments and in some embodiments the oral care implement 200 simply comprises a store of oral care material 281 without the location of the store of oral care material 281 being limiting of the invention. The store of oral care material 281 may be located within the head portion 210 of the oral care implement 200, within the handle portion 220 of the oral care implement 200 or elsewhere as desired.

As noted briefly above, in certain embodiments it is desired that the oral care material 281 has an efficacy that is increased or activated by the EMR generated by the EMR source 265. Thus, after a user applies the oral care material 281 to his or her teeth, the user can use the treatment device 260 in the manner described above with regard to the treatment device 160 to emit EMR to the user's teeth to increase the efficacy of the oral care material 281 or to activate the oral care material 281.

The oral care material may be any type of material that is desired to apply to a user's teeth and or other oral surfaces in order to impart benefits to the user's teeth and other oral surfaces. In one embodiment, the oral care material is a tooth whitening agent or solution. In such embodiments any suitable tooth whitening agent can be used, including without limitation peroxide containing tooth whitening compositions. Other whitening agents may include an oxidizer such as for example without limitation carbamide peroxide, carbamyl peroxide, sodium percarbonate, perhydrol urea, peroxyacetic acid, and hydrogen peroxide.

While a tooth whitening agent is one of the preferred oral care materials in the present invention, other oral care materials can be used with the invention. Contemplated oral care materials include without limitation, antibacterial agents; oxidative or whitening agents; enamel strengthening or repair agents; tooth erosion preventing agents; tooth sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof. The oral care material, however, is preferably free of (i.e., is not) toothpaste in some embodiments. Instead, the oral care material is intended to provide benefits in addition to merely brushing one's teeth. Furthermore, regardless of the exact oral care material selected to be used with the oral care implement 200, the oral care material has an efficacy that is increased or activated by EMR generated by the EMR source 265.

In addition to having the internal cavity 280 for storing the oral care material 281, the oral care implement 200 also includes an applicator 285 that is coupled to the body 205. The applicator 285 is fluidly coupled to the store of oral care material 281 so that the oral care material 281 can be easily dispensed through the applicator 285 directly to a user's teeth and/or other oral surfaces. More specifically, the applicator 285 comprises a dispensing orifice 286 that provides a passageway from the store of oral care material 281 to a dispensing surface 287 of the applicator 285.

In the exemplified embodiment, the applicator 285 is formed out of a resilient material, such as a thermoplastic elastomer or other rubber-like material. Of course, the invention is not to be so limited in all embodiments and the applicator 285 can be formed of other materials in other embodiments. Forming the applicator 285 out of a thermoplastic elastomer or other resilient material increases the comfort to a user when the applicator 285 is used to dispense the oral care material 281 to the user's teeth or other oral surfaces. Specifically, in use the applicator 285 is made to directly contact the user's teeth or other oral surfaces upon which it is desired to dispense and/or apply the oral care material 281. Using a soft or resilient material reduces the likelihood of injury to the user during this dispensing.

In the exemplified embodiment, the applicator 285 further includes a plurality of protuberances 288 extending from the dispensing surface 287. Such protuberances 288 may further increase the ability to apply and wipe the oral care material 281 directly to the desired surface. Of course, in other embodiments the protuberances 288 may be omitted and the dispensing surface 287 of the applicator 285 may be a planar surface that is either flat or angled/inclined as illustrated.

In the exemplified embodiment, the applicator 285 extends or protrudes from the proximal end 221 of the handle portion 220 of the body 205. Of course, the invention is not to be so limited and the applicator 285 can be positioned at other locations on the oral care implement 200 as desired. However, positioning the applicator 285 so as to extend from the proximal end 221 of the handle portion 220 of the body 205 facilitates ease of use of the applicator 285 for dispensing the oral care material 281.

Furthermore, in the exemplified embodiment the oral care implement 200 includes a cap 289 that couples to the proximal end 221 of the handle portion 220 of the body 205 to cover and protect the applicator 285 when the applicator 285 is not being used. The cap 289 preferably conforms to the shape of the handle portion 220 of the body 205 so that when the cap 289 is coupled to the handle portion 220 of the body 205 a smooth continuous surface is formed that is free of ridges, bumps and other undulations to enhance user comfort when the user is manipulating the handle portion 220. Of course, the cap 289 is not necessary in all embodiments and it may be omitted if desired.

Although described herein with the oral care material 281 stored within the internal cavity 280 of the body 205, the invention is not to be so limited in all embodiments. In certain embodiments the oral care material 281 can be stored within a separate dispenser that is detachably coupled to the body 205. The dispenser may be stored within the body 205 or otherwise attached to the body 205. In such embodiments, the dispenser may comprise an applicator comprising a dispensing orifice for dispensing the oral care material 281 to the user's teeth and/or other oral surfaces.

When it is desired to use the treatment device 260, the treatment device 260 is transitioned from the storage state to the use state whereby the treatment device 260 may be detached from the body 205, or may be hingedly or otherwise attached to the body 305 but accessible for use. First, the applicator 285 of the body 205 is positioned against the user's teeth or other oral surfaces to dispense the oral care material 281 onto the user's teeth or other oral surfaces. After the desired amount of the oral care material 281 has been dispensed onto the user's teeth or other oral surfaces, the inner surface 267 of the housing 261 of the treatment device 260 is positioned adjacent to the user's teeth to emit the EMR onto the user's teeth that have been pre-coated with the oral care material. The EMR will improve the efficacy of the oral care material 281 to speed up or increase the beneficial result achieved by the oral care material 281 (such as tooth whitening). After the EMR has been applied for a desired amount of time, the treatment device 260 is placed back into the storage state. Once in the storage state, the switch 266 is automatically opened (or can be manually opened in other embodiments) and the EMR source 265 no longer emits the EMR. These steps can be repeated for as many uses as desired.

Referring to FIGS. 8-11 concurrently, an oral care implement 300 will be described in accordance with yet another embodiment of the present invention. Again, the oral care implement 300 is similar to the oral care implement 100 in many respects, and thus similar features will be similarly numbered except that the 300-series of numbers will be used. Certain features of the oral care implement 300 may be similarly numbered as the oral care implement 100 but might not be described in detail herein in the interest of brevity, it being understood that the discussion of the similar component on the oral care implement 100 applies. Furthermore, features of the oral care implement 100 described above that are not illustrated on the oral care implement 300 or that are illustrated on the oral care implement 300 but not numbered are applicable to the oral care implement 300 in certain embodiments and vice versa. Thus, various combinations of the description below with regard to the oral care implement 300 and the description above with regard to the oral care implements 100, 200 are within the scope of the present invention in some embodiments.

The oral care implement 300 generally comprises a body 305 having a handle portion 320 and a head portion 310 with tooth cleaning elements 315 extending from the head portion 310. More specifically, the handle portion 320 extends from a proximal end 321 to a distal end 322 along a longitudinal axis C-C, and the head portion 310 is coupled to the distal end 322 of the handle portion 320. Furthermore, the oral care implement 300 also comprises a treatment device 360 that is coupled to the body 305. The treatment device 360 is similar to the treatment device 160 and comprises a housing 361 that contains a power source 364, a controller or processor 370, a switch 366 and an EMR source 365 that are operably coupled together. The EMR source 365 comprises a first EMR source portion 365A and a second EMR source portion 365B that emit EMR 399 through a first EMR transmissive portion 369A and a second EMR transmissive portion 369B on the housing 361. The treatment device 360 also includes a bite guard 368 that extends from an inner surface 367 of the housing 361. The treatment device 360 operates in a similar manner to the treatment device 160 as discussed above.

Figure 11:
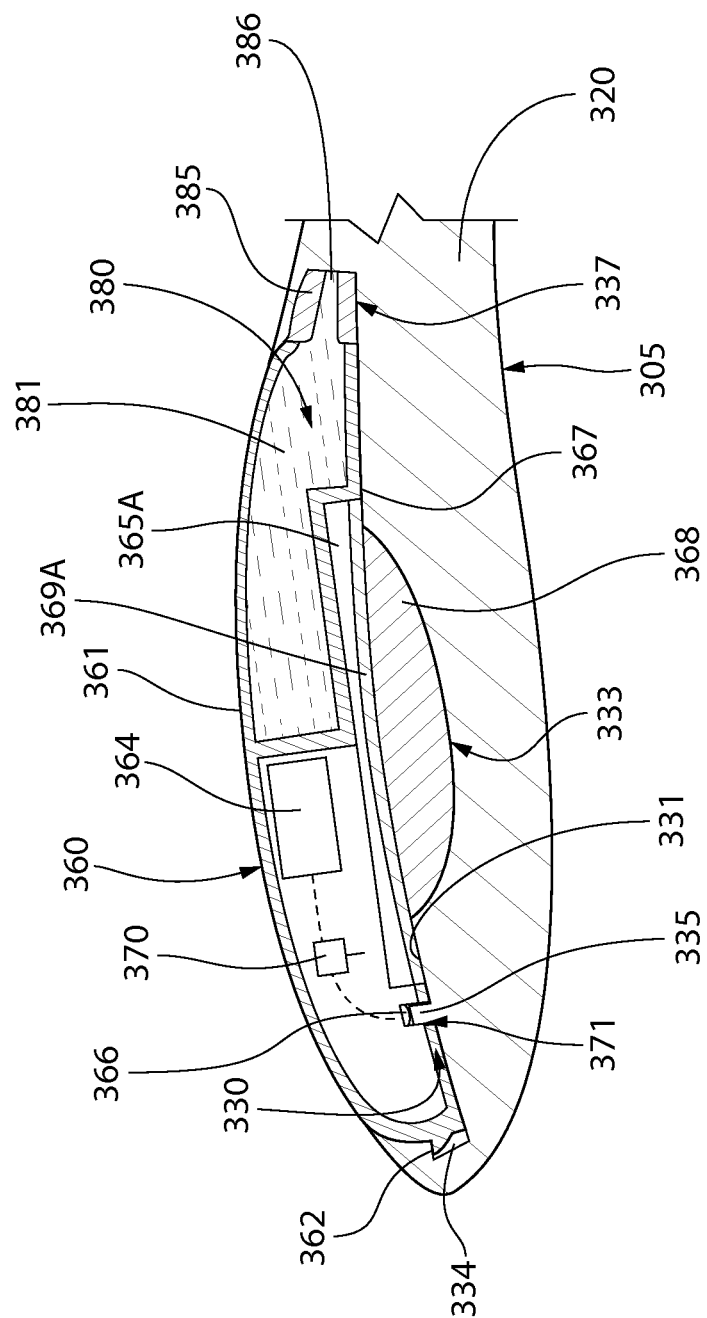
FIG. 11 is a schematic cross-sectional view taken along line XI-XI of FIG. 8 with the treatment device coupled to the body.

The body 305 of the oral care implement 300 comprises a longitudinal depression 330 having a floor 331. In this embodiment, the floor 331 of the longitudinal depression 330 has a convex surface that mates with a concave inner surface 367 of the treatment device 360 as discussed in more detail below. An aperture 333 is formed into the floor 331 of the longitudinal depression 330 for accommodating the bite guard 368 of the treatment device 360 when the treatment device 360 is in the storage state (FIG. 11). Furthermore, a protuberance 335 extends upwardly from the floor 331 of the longitudinal depression 330 for mating with an opening 371 and switch 366 on the treatment device 360 in much the same manner as discussed above with regard to the oral care implement 100. The treatment device 360 is coupled to the body 305 in a manner similar to that described above with regard to the treatment device 160. Specifically, the treatment device 360 has a connector 362 and the longitudinal depression 330 has a connector 334 that mate with one another when the treatment device 360 is in the storage state. However, the body 305 of the oral care implement 300 also includes a cavity 337 that houses an applicator 385 of the treatment device 360 as discussed below.

In addition to housing the power source 364, the EMR source 365, the processor 370 and the switch 366, the treatment device 360 also comprises a reservoir or internal cavity 380 for storing a store of oral care material 381. The oral care material 381 can be any of the oral care materials 281 discussed above such that the efficacy of the oral care material 381 is increased or activated by EMR generated by the EMR source 365. The internal features of the treatment device 360 include a wall 369 that separates the internal cavity 380 from the electronic components (i.e., the power source 364, the EMR source 365, the processor 370 and the switch 366). Thus, despite containing the oral care material 381, the electronic components of the treatment device 360 are protected against liquid/water damage by the wall 369. Stated another way, the wall 369 isolates the internal cavity 380 and hence also the oral care material 381 from the electronic components.

Additionally, the treatment device 360 also comprises an applicator 385 that is fluidly coupled to the oral care material 381 contained within the internal reservoir 380. Specifically, the applicator 385 comprises a dispensing orifice 386 that forms a passageway from the internal cavity 380 to a dispensing surface 387 of the applicator 385. The applicator 385 is preferably formed of a resilient material such as a thermoplastic elastomer as discussed above with regard to the applicator 285. The applicator 385 can be used to directly contact the user's teeth and/or other oral surfaces to directly apply the oral care material 381 to the user's teeth and/or other oral surfaces. In some embodiments the dispensing action can be achieved by squeezing the housing 361 of the treatment device 360. In such embodiments, the housing 361 of the treatment device 360, or portions thereof that surround the internal cavity 380, may be formed of a resilient and depressible material (i.e., a thin plastic, a thermoplastic elastomer or the like). In other embodiments the treatment device 360 may include a pump mechanism for pumping the oral care material 381 from the internal reservoir 380 through the applicator 385 for dispensing as desired. Of course, other techniques for dispensing the oral care material 381 are possible.

As noted above, in this embodiment the inner surface 367 of the housing 361 of the treatment device 360 is concave. This is done so that the inner surface 367 of the housing 361 of the treatment device 360 has a shape that corresponds with the shape and/or curvature of a user's teeth. Thus, when the treatment device 360 is held up to a user's teeth as has been discussed above, the inner surface 367 of the housing 361 of the treatment device 360 will be aligned with the user's teeth so that the EMR 399 generated/emitted by the EMR source 365 of the treatment device 360 will be directed onto the user's teeth. Any of the embodiments of the treatment devices discussed herein can include the concave inner surface.

Figure 8:
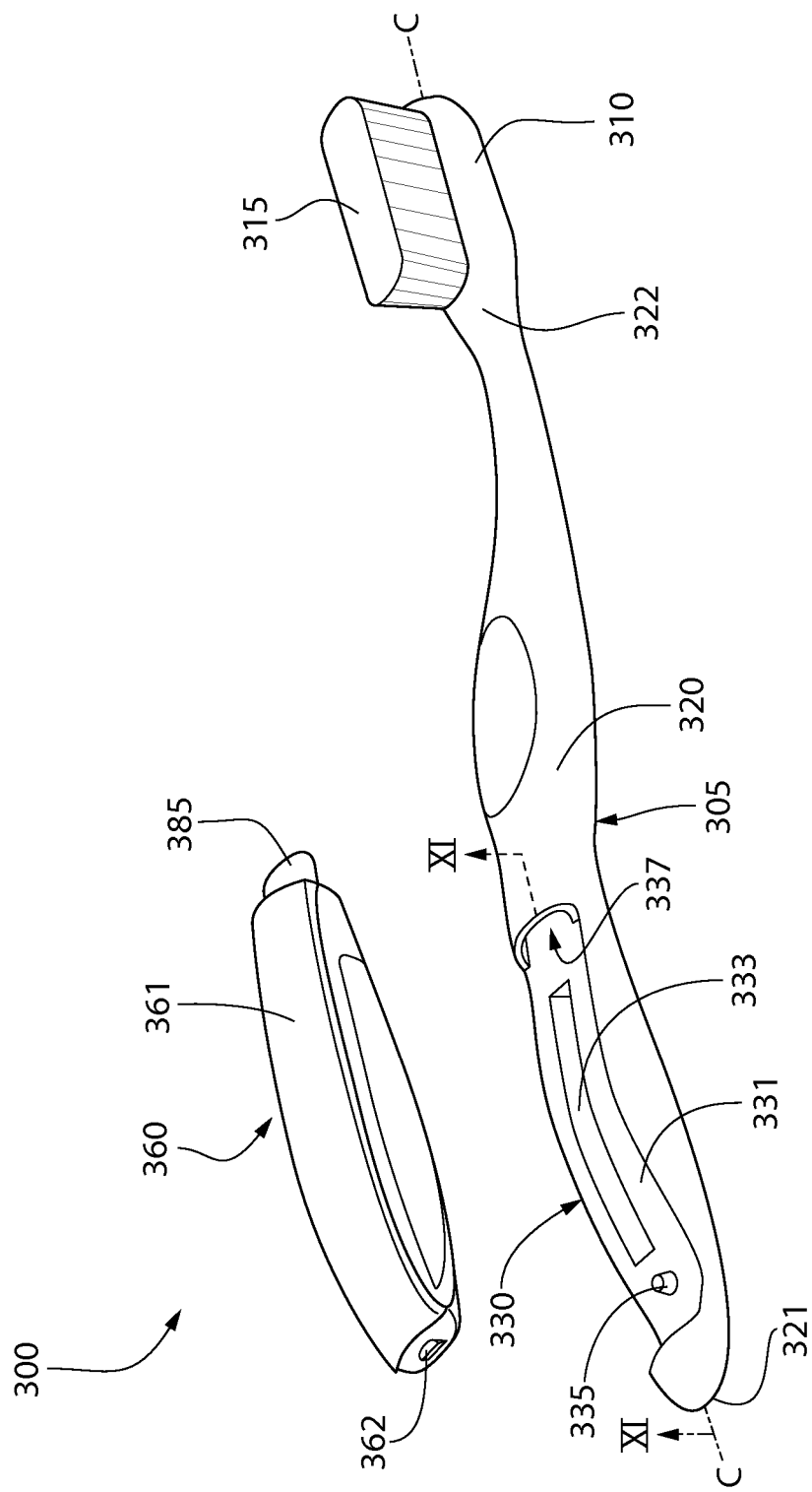
FIG. 8 is a perspective view of a toothbrush having a body and a treatment device separated therefrom in accordance with a third embodiment of the present invention.
Figure 9:
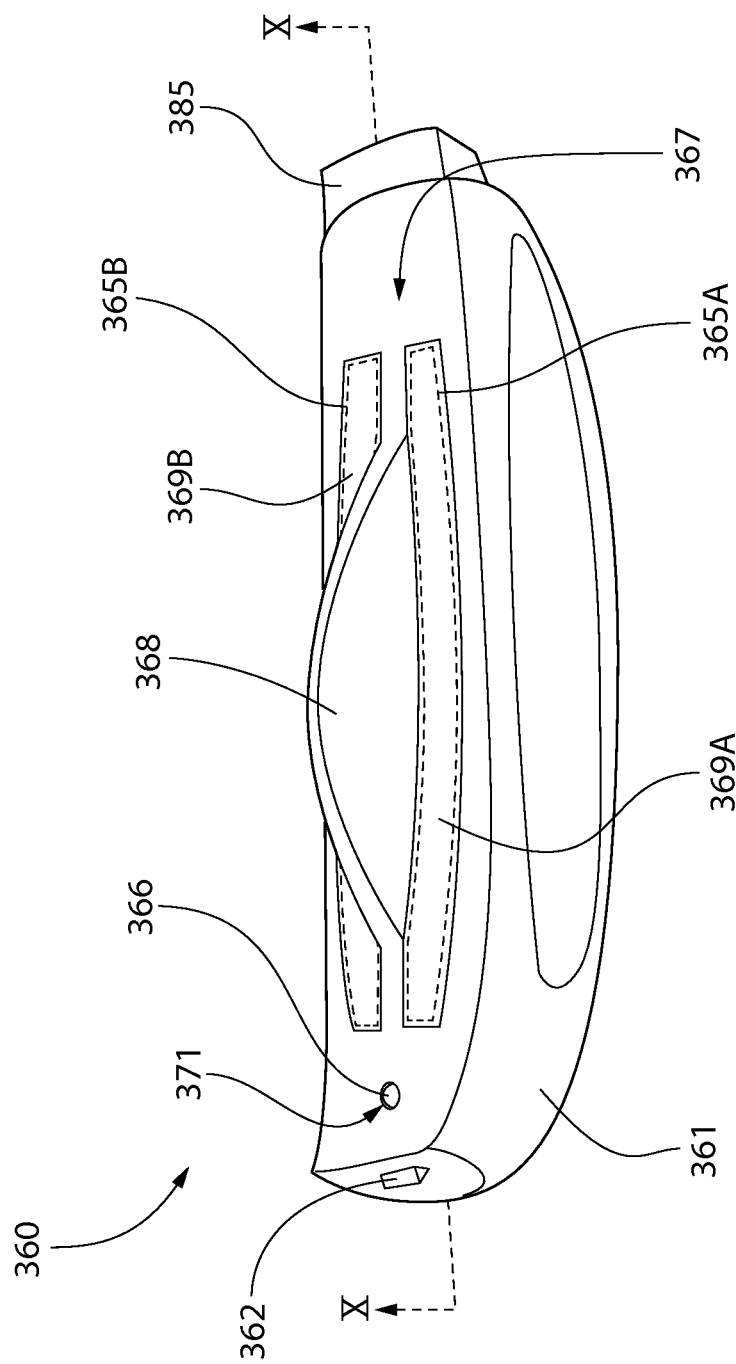
FIG. 9 is a perspective view of the treatment device of FIG. 8.
Figure 10:
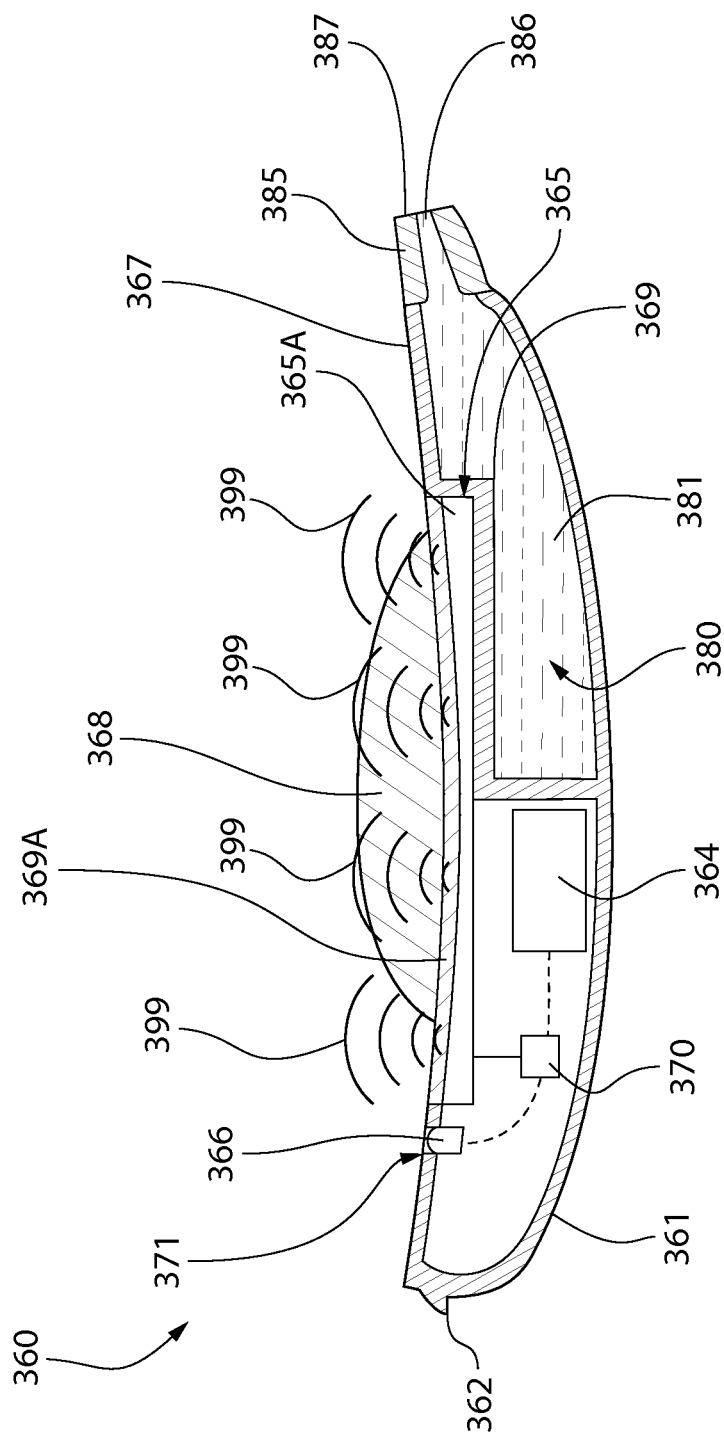
FIG. 10 is a schematic cross-sectional view taken along line X-X of FIG. 9.

When the treatment device 360 is in the storage state as illustrated in FIG. 11, the treatment device 360 is disposed within the longitudinal depression 330 on the body 305 of the oral care implement 300 so that the inner surface 367 of the treatment device 360 is embedded in the handle portion 320 (i.e., unexposed and not visible). Furthermore, the bite guard 368 of the treatment device 360 extends into the aperture 333 in the longitudinal depression 330. Additionally, the protuberance 335 on the longitudinal depression 330 extends into the opening 371 and contacts the switch 366 so as to open the switch. In this way, the EMR source 365 is powered off because the switch is open 366 when the treatment device 360 is in the storage state. However, as discussed above when the treatment device 360 is in the use state (such as by being detached from the body 305 as illustrated in FIG. 8), the switch 366 automatically closes so that the EMR source 365 is powered on and emitting the EMR 399. Of course, other types of switches can be used that are not automated in other embodiments.

Furthermore, when the treatment device 360 is in the storage state, the connector 362 of the treatment device 360 mates with the connector 334 of the longitudinal depression 330. Furthermore, the applicator 385 of the treatment device 360 extends into the cavity 337 in the body 305 of the oral care implement 300. Thus, the applicator 385 is protected against damage when the treatment device 360 is in the storage state. Although not illustrated, in some embodiments there may be a closure pin extending into the cavity 337 from a rear wall of the cavity 337 that closes the dispensing orifice 386 of the applicator 385 when the treatment device 360 is in the storage state. Such a closure pin may prevent leakage of the oral care material 381 during storage of the treatment device 360.

When it is desired to use the treatment device 360, the treatment device 360 is transitioned from the storage state to the use state whereby the treatment device 360 may be detached from the body 305, or may be hingedly or otherwise attached to the body 305 but accessible for use. First, the applicator 385 of the treatment device 360 is positioned against the user's teeth or other oral surfaces to dispense the oral care material 381 onto the user's teeth or other oral surfaces. After the desired amount of the oral care material 381 has been dispensed onto the user's teeth or other oral surfaces, the inner surface 367 of the housing 361 of the treatment device 360 is positioned adjacent to the user's teeth to emit the EMR 399 onto the user's teeth that have been pre-coated with the oral care material. The EMR 399 will improve the efficacy of the oral care material 381 to speed up or increase the beneficial result achieved by the oral care material 381 (such as tooth whitening). After the EMR 399 has been applied for a desired amount of time, the treatment device 360 is placed back into the storage state. Once in the storage state, the switch 366 is automatically opened (or can be manually opened in other embodiments) and the EMR source 365 no longer emits the EMR 399. These steps can be repeated for as many uses as desired.

In certain embodiments, the internal reservoir 380 can be refillable so that upon depletion of the oral care material 381 from the internal reservoir 380, more of the oral care material 381 can be added to the internal reservoir 380. Of course, the invention is not to be so limited in all embodiments and in certain other embodiments the internal reservoir 380 may not be refillable such that upon depletion of the oral care material 381 the treatment device 360 may be disposed. In some embodiments the EMR source 365 or the power source 364 may have a life-span that matches that of the oral care material 381 so that upon depletion of the oral care material 381 the EMR source 365 and/or the power source 364 would also need to be replaced, in which case it may be desirable to replace the entire treatment device 360.

Figure 12:
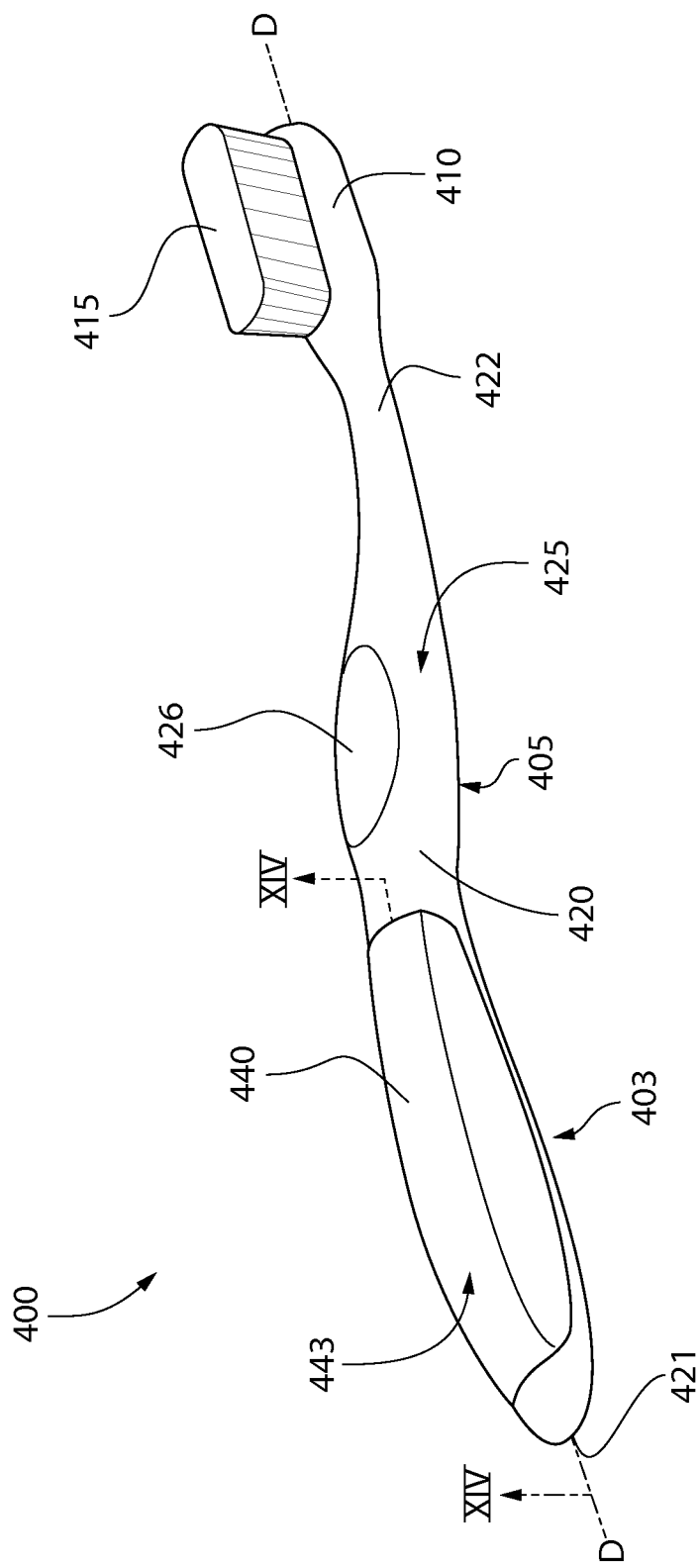
FIG. 12 is a perspective view of a toothbrush having a body and a cover coupled thereto in accordance with a fourth embodiment of the present invention.
Figure 13:
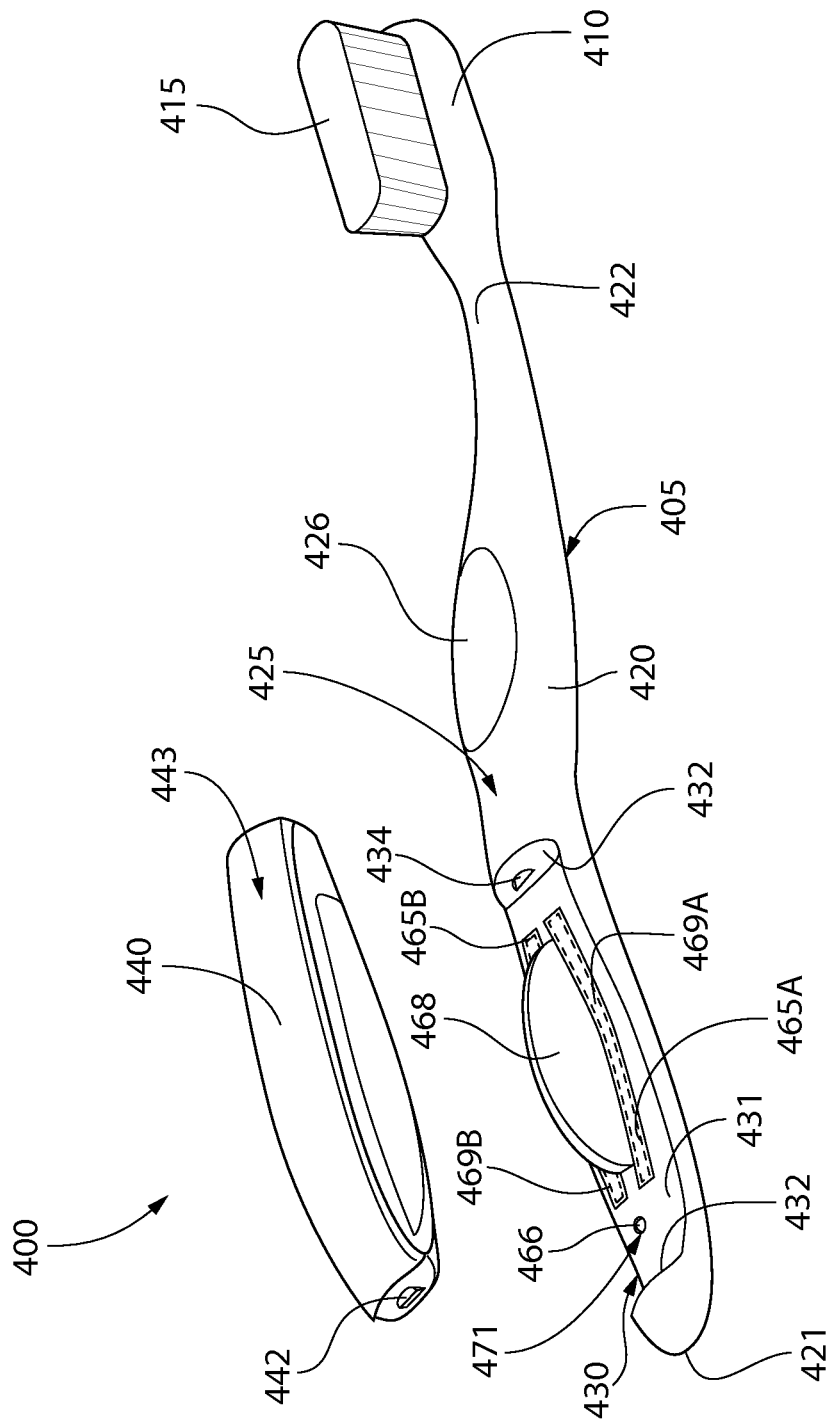
FIG. 13 is a perspective view of the toothbrush of FIG. 12 with the cover separated from the body.
Figure 14:
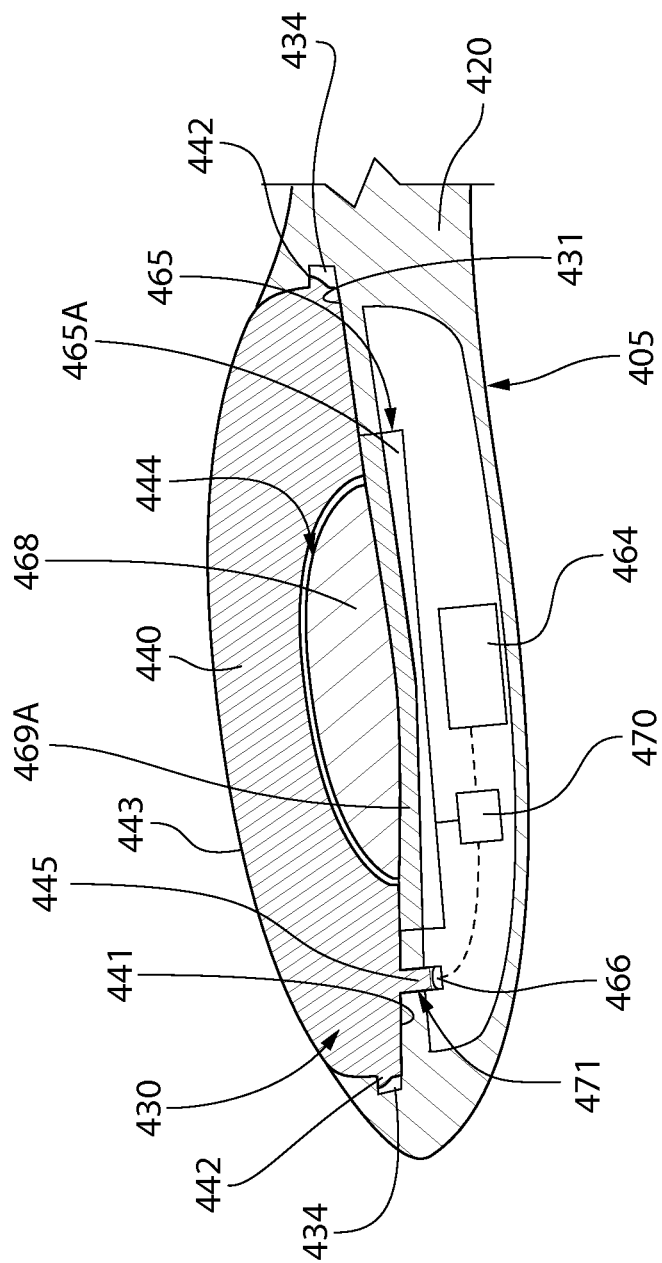
FIG. 14 is a schematic cross-sectional view taken along line XIV-XIV of FIG. 12 in accordance with one embodiment of the present invention.

Referring now to FIGS. 12-14 concurrently, an oral care implement 400 will be described in accordance with yet another embodiment of the present invention. The oral care implement 400 is similar to the oral care implement 100 in many respects, and thus similar features will be similarly numbered except that the 400-series of numbers will be used. Certain features of the oral care implement 400 may be similarly numbered as the oral care implement 100 but might not be described in detail herein in the interest of brevity, it being understood that the discussion of the similar component on the oral care implement 100 applies. Furthermore, features of the oral care implement 100 described above that are not illustrated on the oral care implement 400 or that are illustrated on the oral care implement 400 but not numbered are applicable to the oral care implement 400 in certain embodiments and vice versa. Thus, various combinations of the description below with regard to the oral care implement 400 and the description above with regard to the oral care implements 100, 200, 300 are within the scope of the present invention in some embodiments.

The main difference between the oral care implement 400 and the oral care implement 100 is that in the oral care implement 400 the components of the treatment device of the oral care implement 100, such as the power source, the EMR source, the switch and the like, are located on a depression that is formed into the body of the oral care implement 400. The general features and use of the oral care implement 400 is otherwise similar to that of the oral care implement 100 that has been described above.

The oral care implement 400 generally comprises a body 405 having a handle portion 420 and a head portion 410. The handle portion 420 extends from a proximal end 421 to a distal end 422 along a longitudinal axis D-D, and the head portion 410 is coupled to the distal end 422 of the handle portion 420. The handle portion 420 of the oral care implement 400 has an outer surface 425 that includes the front and rear surfaces thereof. A plurality of tooth cleaning elements 415 extend from the head portion 410 of the oral care implement 400.

The oral care implement 400 further comprises a depression 430 formed into the outer surface 425 of the handle portion 420, the depression 430 having a floor 431 and upstanding sidewalls 432 extending from the floor 431 to the outer surface 425 of the handle portion 420. The depression 430, in the exemplified embodiment, is located on the front surface of the handle portion 420 near the proximal end 421 of the handle portion 420, and more specifically in a proximal region 403 of the handle portion 420 that is between the proximal end 421 of the handle portion 420 and a thumb grip region 426 of the handle portion 420. Of course, the invention is not to be so limited and the depression 430 can be otherwise located along the handle portion 420. In the exemplified embodiment, the depression 430 is longitudinally elongated such that it extends axially with the longitudinal axis D-D.

In the exemplified embodiment, the floor 431 of the depression 430 is concave. Thus, the floor 431 of the depression 430 has a shape that corresponds with the shape of a user's teeth. The benefits of this will be appreciated from the discussion of the use of the oral care implement 400 to emit EMR to a user's teeth and other oral surfaces as discussed below.

The oral care implement 400 further comprises a power source 464 disposed within the body 405 and an electromagnetic radiation (EMR) source 465 disposed within the handle portion 420. More specifically, the EMR source 465 is located within the handle portion 420 at a position along the depression 430. The EMR source 465 is operably coupled to the power source 464 to provide power to the EMR source 465. More specifically, in the exemplified embodiment the power source 464 and the EMR source 465 are both operably coupled to a controller or processor 470, although the processor 470 may be omitted in other embodiments. When power is being provided to the EMR source 465, the EMR source 465 emits EMR. Furthermore, due to the positioning of the EMR source 465, when power is provided to the EMR source 465, the EMR source emits EMR from the floor 431 of the depression 430.

In the exemplified embodiment, the oral care implement 400 further comprises a bite guard 468 protruding from the floor 431 of the depression 430. Furthermore, a first EMR transmissive portion 469A and a second EMR transmissive portion 469B are located adjacent to the bite guard 468. The EMR source 465 includes a first EMR source portion 465A positioned beneath and adjacent to the first EMR transmissive portion 469A and a second EMR source portion 465B positioned beneath and adjacent to the second EMR transmissive portion 469B. Thus, when the EMR source portion 465 is powered on, EMR is emitted from the first EMR source portion 465A through the first EMR transmissive portion 469A and from the second EMR source portion 465B through the second EMR transmissive portion 469B.

In the exemplified embodiment, the bite guard 468 is a semi-circle shaped feature that extends along the longitudinal axis D-D. Furthermore, each of the first and second EMR source portions 465A, 465B are also elongated along the longitudinal axis adjacent to the bite guard 468 such that the bite guard 468 is positioned in between the first and second EMR source portions 465A, 465B. Although illustrated as being semi-circle shaped, the invention is not to be so limited and the bite guard 468 can take on any other shape such as those described above with regard to the bite guard 168. Furthermore, the bite guard 468 can be formed integrally with the body 405 of the oral care implement 400 out of a rigid plastic material such as those described above, or the bite guard 468 may be formed of a thermoplastic elastomer and then later coupled to the body 405 of the oral care implement 400. Furthermore, in some embodiments the bite guard 468 may be altogether omitted.

An opening 471 is formed into the floor 431 of the depression 430 and a switch 466 is positioned within the opening 471. When the switch 466 is in a closed state, power is supplied from the power source 464 to the EMR source 465 so that the EMR source 465 emits EMR from the floor 431 of the depression 430. When the switch 466 is in an open state, power is prevented from being supplied to the EMR source 465 so that EMR is not emitted from the EMR source 465. The switch 466 may be one which is biased into a closed state such as the switch 166 discussed above.

The oral care implement 400 also comprises a cover 440 that is coupled to the handle portion 420. The cover 440 is alterable between a storage state in which the depression 430 is enclosed by the cover (FIG. 12) and a use state in which the floor 431 of the depression 430 is exposed (FIG. 13). The cover 440 comprises a connector 442 that correspondingly mates with a connector 434 on the sidewalls 432 of the depression 430 when the cover 440 is coupled to the handle portion 420 in the storage state. When the cover 440 is in the use state as illustrated in FIG. 13, the switch 466 is in a closed state and EMR is being emitted from the EMR source 465 through the floor 431 of the depression 430. Of course, the switch need not be one which is biased into a closed state in all embodiments and other types of switches can be used such as press button switches, slide switches and the like.

The cover 440 has an inner surface 441 and an outer surface 443. An aperture 444 is formed into the inner surface 441 of the cover 440. Furthermore, a protuberance 445 protrudes from the inner surface 441 of the cover 440. When the cover 440 is in the storage state (see FIGS. 12 and 14), the bite plate 468 is disposed within the aperture 444 of the cover 440 and the protuberance 445 of the cover 440 extends into the opening 471 in the floor 431 of the depression 430 so as to contact the switch 466. More specifically, the protuberance 445 transitions the switch 466 from the biased closed state to an open state whereby power is not supplied to the EMR source 465 and EMR is therefore not emitted by the EMR source 465. Thus, when the cover 440 is in the storage state, the EMR is not being emitted.

The oral care implement 400 can be used as follows. The tooth cleaning elements 415 on the oral care implement 400 can be used to brush a user's teeth in a conventional manner. Before or after brushing or at any other desired time, an oral care material, such as any of the oral care materials discussed above, can be applied to the user's teeth or other oral surfaces. After the oral care material is applied to the user's teeth or other oral surfaces, the cover 440 can be altered from the storage state into the use state. This can be achieved by completely separating the cover 440 from the body 405 as depicted in the exemplified embodiment, or by otherwise moving the cover 440 so as to expose the floor 431 of the depression 430.

Once the floor 431 of the depression 430 is exposed, the floor 431 of the depression 430 is positioned adjacent to a user's teeth. This can be achieved by a user simply holding the body 405 of the oral care implement 400 so that the floor 431 of the depression 430 is adjacent to a user's teeth. In other embodiments, the user may grip the bite guard 468 between his or her teeth in order to maintain the floor 431 of the depression 430 adjacent to and aligned with the user's teeth. As noted above, upon altering the cover 440 into the use state, the switch 466 will be automatically closed (or can be manually closed by a user pressing a button switch or sliding a slide switch). When the switch 466 is closed, the EMR source 465 is powered and begins to emit EMR from the floor 431 of the depression 430. Thus, when the cover 440 is in the use state and the floor 431 of the depression 430 is positioned adjacent to a user's teeth, the EMR is being emitted directly onto the user's teeth. Thus, the benefits of the EMR combined with the desired oral care material can be imparted to the user using the oral care implement 400.

When the cover 440 is in the storage state, the outer surface 425 of the handle portion 420 is substantially flush with the outer surface 443 of the cover 440. This results in a smooth, continuous outer surface of the handle to be gripped by a user during manipulation of the oral care implement 400 during use to prevent injury to the user's hand and enhance comfort.

Figure 15:
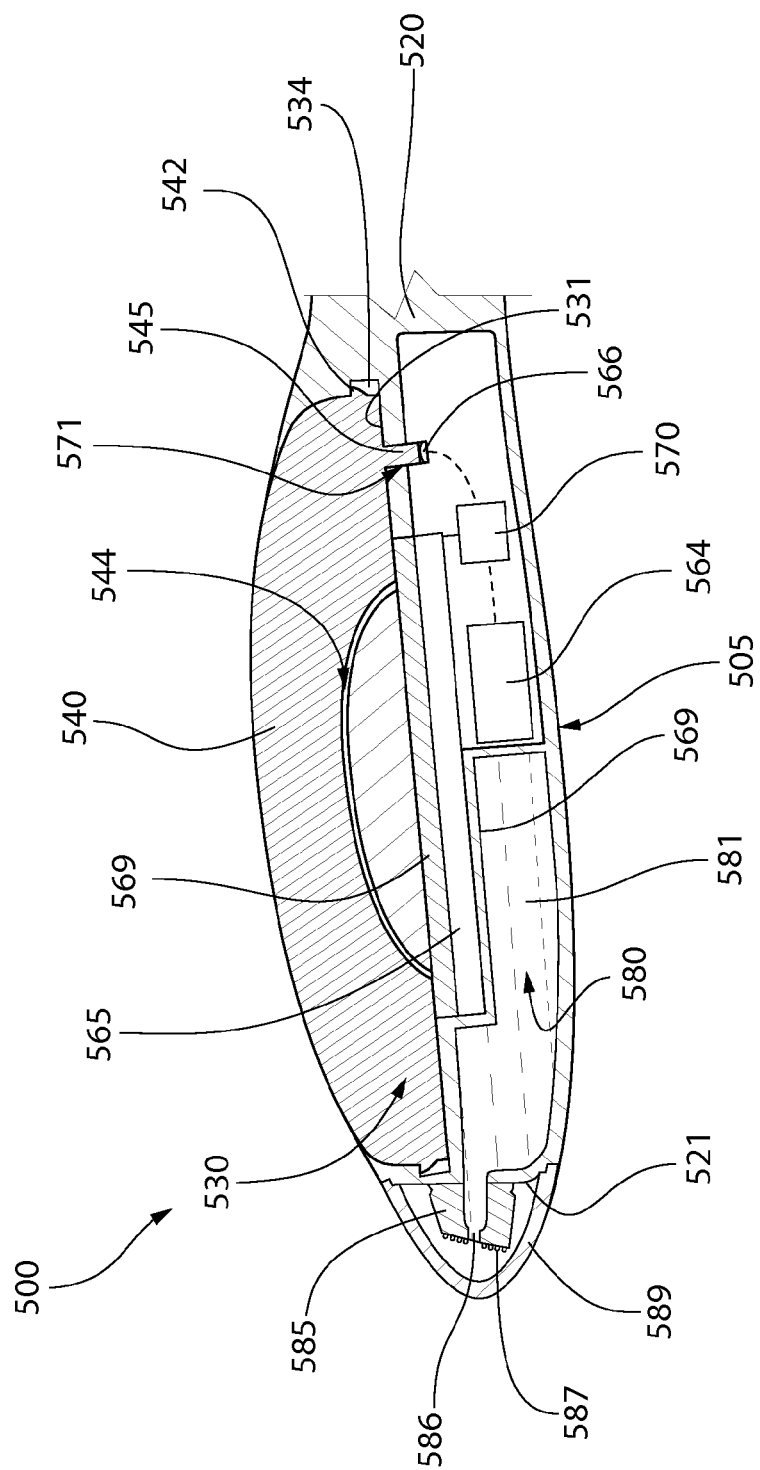
FIG. 15 is a schematic cross-sectional view taken along line XIV-XIV of FIG. 12 in accordance with another embodiment of the present invention.

Referring now to FIG. 15, an oral care implement 500 will be described in accordance with yet another embodiment of the present invention. The oral care implement 500 is similar to the oral care implement 400 in terms of general structure, but has some modifications and additions. Thus, the oral care implement 500 is similar to the oral care implement 400 in many respects, and thus similar features will be similarly numbered except that the 500-series of numbers will be used. Certain features of the oral care implement 500 may be similarly numbered as the oral care implement 400 but might not be described in detail herein in the interest of brevity, it being understood that the discussion of the similar component on the oral care implement 400 applies. Furthermore, features of the oral care implement 400 described above that are not illustrated on the oral care implement 500 or that are illustrated on the oral care implement 500 but not numbered are applicable to the oral care implement 500 in certain embodiments and vice versa. Thus, various combinations of the description below with regard to the oral care implement 500 and the description above with regard to the oral care implements 100, 200, 300, 400 are within the scope of the present invention in some embodiments.

In FIG. 15, a schematic cross-sectional view of the oral care implement 500 is illustrated, similar to the schematic cross-sectional view depicted in FIG. 14. Thus, the features of the oral care implement 500 that are not illustrated are the same as the features of the oral care implement 400 and will not be described below in the interest of brevity.

Of those features that are depicted, the oral care implement 500 comprises a body 505 that includes a handle 520. A power source 564, a controller or processor 570, a switch 566 and an EMR source 565 are disposed within the body 505. The power source 565, the processor 570, switch 566 and EMR source 565 are operably coupled together in the manner that has been discussed above to enable the EMR source 565 to emit EMR when the switch 566 is closed and to prevent the EMR source 565 from emitting EMR when the switch 566 is open.

In addition to those electronic components, the oral care implement 500 also comprises a store of oral care material 581. The store of oral care material 581 is preferably an oral care material, such as any of the oral care materials discussed above, that has an efficacy that is increased or activated by EMR. In the exemplified embodiment, the store of oral care material 581 is disposed within an internal cavity 580 of the body 505 of the oral care implement 500. However, the invention is not to be so limited in all embodiments and in certain other embodiments the store of oral care material 581 can be disposed within a dispenser that is detachably coupled to the body.

In the exemplified embodiment, as noted above, the oral care implement 500 comprises an internal cavity 580 that houses or contains the oral care material 581. A wall 569 is provided within the body 505 of the oral care implement 500 that seals off the internal cavity 580 from the electronic components to prevent the oral care material 581 from damaging the electronic components. Furthermore, in the exemplified embodiment an applicator 585 is coupled to the body 505 so as to be fluidly coupled with the oral care material 581 housed within the internal cavity 580. In that regard, the applicator 585 comprises a dispensing orifice 586 that creates a passageway from the oral care material 581 to a dispensing surface 587 of the applicator 585. The applicator 585 can be formed of a thermoplastic elastomer or any other material as discussed above with regard to the applicator 285. The oral care implement 500 further includes a cap 589 that covers the applicator 585 when the applicator 585 is not being used to protect the applicator 585 and prevent leakage of the oral care material 581 through the applicator 585.

The oral care implement 500 further includes a cover 540 that is similar in all regards to the cover 440 discussed above. The cover 540 is alterable between a storage state (FIG. 15) and a use state (not illustrated with regard to this particular embodiment, but easily understood from the entirety of the description above). In the storage state, the protuberance 545 of the cover 540 extends into the opening 571 in the floor 531 of the depression 530 to cause the switch 566 to be opened. Furthermore, the connectors 542 on the cover 540 matingly cooperate with the connectors 434 of the body 505 to couple the cover 540 to the body 505 in the storage state.

During use, a user can brush his or her teeth using the oral care implement 500 in the conventional fashion. When it is desired to apply the oral care material 581 to the user's teeth or other oral surfaces, the cap 589 is removed from the body 505 to expose the applicator 585. Then, the applicator 585 is contacted against the user's teeth or other oral surfaces and the oral care material 581 is dispensed directly onto the user's teeth or other oral surfaces. The oral care material 581 may be dispensed by a pump or by manual squeezing of the area of the body 505 that surrounds the internal cavity 580. After the desired amount of the oral care material 581 has been applied to the user's teeth or other oral surfaces, the cover 540 is altered into the use state. The cover 540 may be completely detached from the body 505 in the use state, or it may simply be altered in any manner that exposes the floor 531 of the depression 530. Once the floor 531 of the depression 530 is exposed, the floor 531 of the depression 530 is positioned adjacent to the user's teeth or other oral surfaces. The user may place the bite guard 568 between his or her teeth if desired, or if the bite guard 568 is omitted the user may simply hold the oral care implement 500 in a position so that the floor 531 of the depression 530 is adjacent to his or her teeth. While the oral care implement 500 is maintained in this position, the EMR is being emitted from the EMR source 565. After a desired amount of time has expired, the user can pull the oral care implement 500 away from his or her teeth and replace the cover 540 back onto the body 505 of the oral care implement 500.

Figure 16:
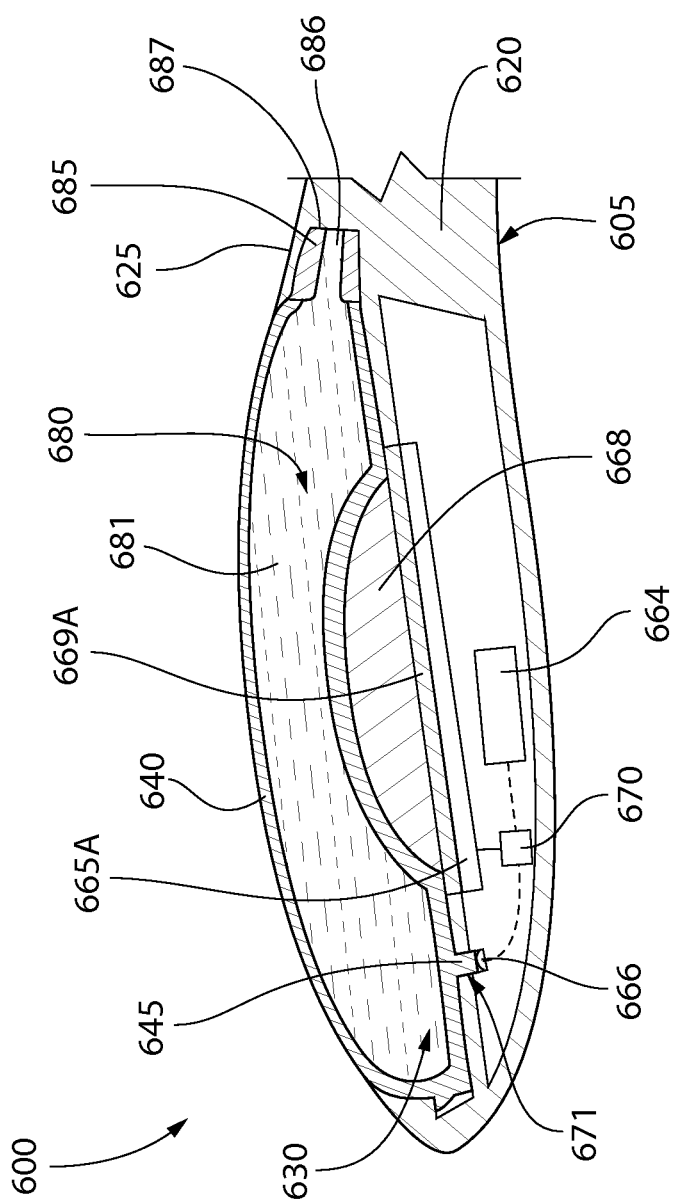
FIG. 16 is a schematic cross-sectional view taken along line XIV-XIV of FIG. 12 in accordance with yet another embodiment of the present invention.

Referring now to FIG. 16, an oral care implement 600 will be described in accordance with yet another embodiment of the present invention. The oral care implement 600 is similar to the oral care implement 400 in terms of general structure, but has some modifications and additions. Thus, the oral care implement 600 is similar to the oral care implement 400 in many respects, and thus similar features will be similarly numbered except that the 600-series of numbers will be used. Certain features of the oral care implement 600 may be similarly numbered as the oral care implement 400 but might not be described in detail herein in the interest of brevity, it being understood that the discussion of the similar component on the oral care implement 400 applies. Furthermore, features of the oral care implement 400 described above that are not illustrated on the oral care implement 600 or that are illustrated on the oral care implement 600 but not numbered are applicable to the oral care implement 600 in certain embodiments and vice versa. Thus, various combinations of the description below with regard to the oral care implement 600 and the description above with regard to the oral care implements 100, 200, 300, 400, 500 are within the scope of the present invention in some embodiments.

In FIG. 16, a schematic cross-sectional view of the oral care implement 600 is illustrated, similar to the schematic cross-sectional view depicted in FIG. 14. Thus, the features of the oral care implement 600 that are not illustrated are the same as the features of the oral care implement 400 and will not be described below in the interest of brevity.

In this embodiment, the oral care implement 600 comprises a body 605 having a handle portion 620 and a head portion (not illustrated). A cover 640 is coupled to the body 605 and alterable between a storage state (illustrated in FIG. 16) and a use state (not illustrated with regard to this particular embodiment but easily understood from the other embodiments described herein). In the oral care implement 600, the power source 664, the controller or processor 670 and the switch 666 are disposed within the body 605 of the oral care implement 600. The main difference between the oral care implement 600 and the oral care implement 500 is that the oral care material 681 is disposed within the cover 640 rather than within the body 605.

Thus, in the oral care implement 600 the cover 640 has a hollow interior that defines an internal cavity 680 for containing the oral care material 681. Furthermore, the cover 640 has an applicator 685 coupled thereto, the applicator 685 being in fluid communication with the oral care material 681. The applicator 685 comprises a dispensing orifice 686 that provides a passageway from the internal cavity 680 to a dispensing surface 687 of the applicator 685.

All other features of the oral care implement 600 are the same as has been described above with regard to the oral care implements 400, 500. Thus, a depression 630 is formed into an outer surface 625 of the handle portion 620 of the body 605, the depression 630 comprising a floor 631. A bite guard 668 protrudes from the floor 631 of the depression 630. Furthermore, an opening 671 is formed into the floor 631 and the switch 666 is disposed within the opening 671. Moreover, a protuberance 645 extends from the cover 640. Thus, when the cover 640 is coupled to the handle portion 620 of the body 605, the protuberance 645 extends into the opening 671 to open the switch 666 in the manner as has been described above.

The oral care implement 600 can be used as follows. The oral care implement 600 can be used to brush a user's teeth in the conventional manner as desired. Furthermore, at desired times, the cover 640 can be moved into the use state such as by being detached from the handle portion 620 of the body 605. Once detached from the handle portion 620 of the body 605, the cover 640 can be used to dispense the oral care material 681 onto the user's teeth or other oral surfaces. Specifically, the applicator 685 can be made to contact the teeth, and then the oral care material 681 can be dispensed directly onto the user's teeth via the applicator 685. After the oral care material 681 is applied to a user's teeth, the floor 631 of the depression 630 can be placed adjacent to the user's teeth so that EMR can be emitted onto the user's teeth from the EMR source 665A through the EMR transmissive portion 669A of the body 605. After a desired period of time has expired, the oral care implement 600 can be moved away from the user's teeth and the cover 640 can be replaced onto the handle portion 620 into the storage state.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A toothbrush comprising:
    a body comprising a handle portion, a head portion and a longitudinal axis;
    a plurality of tooth cleaning elements extending from the head portion;
    a depression formed in an outer surface of the handle portion of the body, the depression comprising a floor;
    a power source disposed within the body;
    an electromagnetic radiation (EMR) source disposed within the handle portion and operably coupled to the power source, the EMR source configured to emit EMR from the floor of the depression; and
    a cover coupled to the handle portion so as to be alterable between: (1) a storage state in which the depression is enclosed by the cover; and (2) a use state in which the floor of the depression is exposed.

2. The toothbrush according to claim 1 wherein the depression is longitudinally elongated.

3. The toothbrush according to claim 1 wherein the floor of the depression is concave.

4. The toothbrush according to claim 1 wherein an outer surface of the handle portion is substantially flush with an outer surface of the cover when the cover is in the storage state.

5. The toothbrush according to claim 1 further comprising a bite guard protruding from the floor of the depression, the EMR source configured to emit EMR from the floor of the depression adjacent the bite guard.

6. The toothbrush according to claim 5 wherein the EMR source comprises a first EMR source portion and a second EMR source portion, the bite guard located between the first and second EMR source portions.

7. The toothbrush according to claim 1 wherein the depression is located in a proximal section of the handle portion, the head portion coupled to a distal end of the handle portion.

8. The toothbrush according to claim 1 further comprising a store of oral care material, wherein the oral care material has an efficacy that is increased or activated by EMR generated by the EMR source.

9. The toothbrush according to claim 8 wherein the store of oral care material is disposed within an internal cavity of the body, the toothbrush further comprising an applicator comprising a dispensing orifice coupled to the body.

10. The toothbrush according to claim 9 wherein the applicator protrudes from a proximal end of the handle portion.

11. The toothbrush according to claim 8 wherein the store of oral care material is disposed in a dispenser that is coupled to the body, the dispenser comprising an applicator comprising a dispensing orifice.

12. The toothbrush according to claim 8 wherein the store of oral care material is disposed in the cover, the cover comprising an applicator comprising a dispensing orifice.

13. The toothbrush according to claim 1 further comprising a switch, the switch operably coupled to the EMR source and the power source to turn the EMR source off and on.

14. The toothbrush according to claim 13 wherein the switch is inaccessible to a user when the cover is in the storage state.

15. The toothbrush according to claim 13 wherein the switch is automatically maintained or actuated to an open state when the cover is in the storage state.

* * * * *